(12) United States Patent
Spenser

(10) Patent No.: US 9,326,852 B2
(45) Date of Patent: *May 3, 2016

(54) METHOD FOR IMPLANTING PROSTHETIC VALVE

(71) Applicant: Benjamin Spenser, Bat Shlomo (IL)

(72) Inventor: Benjamin Spenser, Bat Shlomo (IL)

( * ) Notice: Subject to any disclaimer, the term of this patent is extended or adjusted under 35 U.S.C. 154(b) by 519 days.

This patent is subject to a terminal disclaimer.

(21) Appl. No.: 13/779,913

(22) Filed: Feb. 28, 2013

(65) Prior Publication Data

US 2013/0211509 A1 Aug. 15, 2013

Related U.S. Application Data

(63) Continuation-in-part of application No. 12/803,849, filed on Jul. 8, 2010, now Pat. No. 8,408,214.

(51) Int. Cl.
*A61F 2/24* (2006.01)

(52) U.S. Cl.
CPC ............... *A61F 2/243* (2013.01); *A61F 2/2403* (2013.01); *A61F 2/2436* (2013.01); *A61F 2/2463* (2013.01); *A61F 2/2412* (2013.01); *A61F 2/2433* (2013.01); *A61F 2250/0063* (2013.01)

(58) Field of Classification Search
CPC .......... A61F 2/24; A61F 2/243; A61F 2/2403
USPC ............ 623/2.1–2.19, 904; 128/898
See application file for complete search history.

(56) References Cited

U.S. PATENT DOCUMENTS

| | | | |
|---|---|---|---|
| 5,411,552 A | 5/1995 | Andersen et al. | |
| 5,840,081 A | 11/1998 | Andersen et al. | |
| 6,165,183 A * | 12/2000 | Kuehn | A61B 17/064 606/139 |
| 6,168,614 B1 | 1/2001 | Andersen et al. | |
| 6,575,971 B2 * | 6/2003 | Hauck | A61B 18/1442 606/41 |
| 6,730,118 B2 | 5/2004 | Spenser et al. | |
| 7,510,575 B2 | 3/2009 | Spenser et al. | |
| 7,611,534 B2 | 11/2009 | Kapadia et al. | |
| 7,618,446 B2 | 11/2009 | Andersen et al. | |
| 2004/0092858 A1* | 5/2004 | Wilson | A61F 2/2418 604/9 |
| 2007/0050014 A1* | 3/2007 | Johnson | A61F 2/2475 623/1.24 |
| 2008/0140189 A1* | 6/2008 | Nguyen | A61F 2/2412 623/2.11 |
| 2009/0234318 A1* | 9/2009 | Loulmet | A61B 17/00234 604/500 |
| 2009/0270858 A1* | 10/2009 | Hauck | A61B 18/1442 606/41 |
| 2009/0326648 A1* | 12/2009 | Machold | A61B 17/00234 623/2.37 |

FOREIGN PATENT DOCUMENTS

WO    WO 98/29057    7/1998

* cited by examiner

*Primary Examiner* — Suzette J Gherbi

(74) *Attorney, Agent, or Firm* — Robert G. Lev

(57) ABSTRACT

A method for implanting a prosthetic valve apparatus in a novel location which replaces the function of a native diseased valve after an Alfieri procedure. The prosthetic valve apparatus includes a one way valve and an expandable valve seating. anchoring and securing apparatus in a newly created orifice near or at the center of the anterior valve leaflet. The prosthetic valve apparatus also causes the sealing of the native valve and thus results in a solution for paravalvular leakage and regurgitation.

20 Claims, 21 Drawing Sheets

PRIOR ART

PRIOR ART

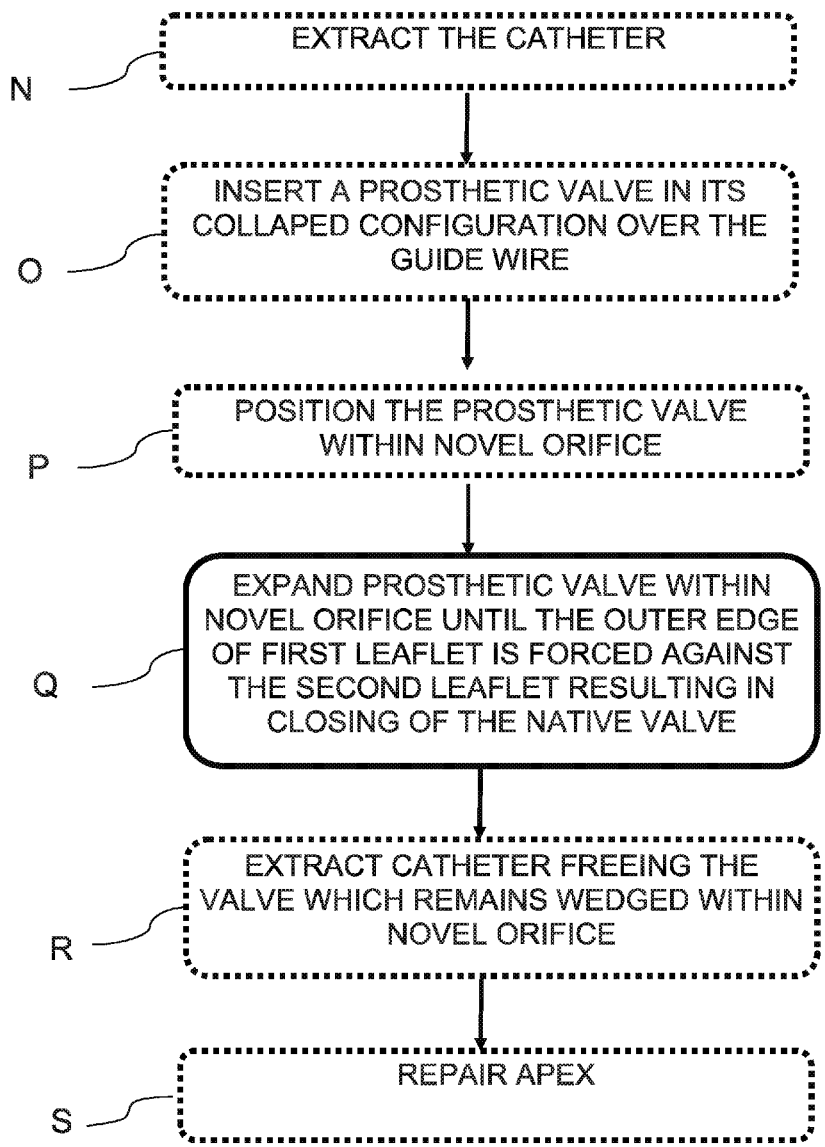

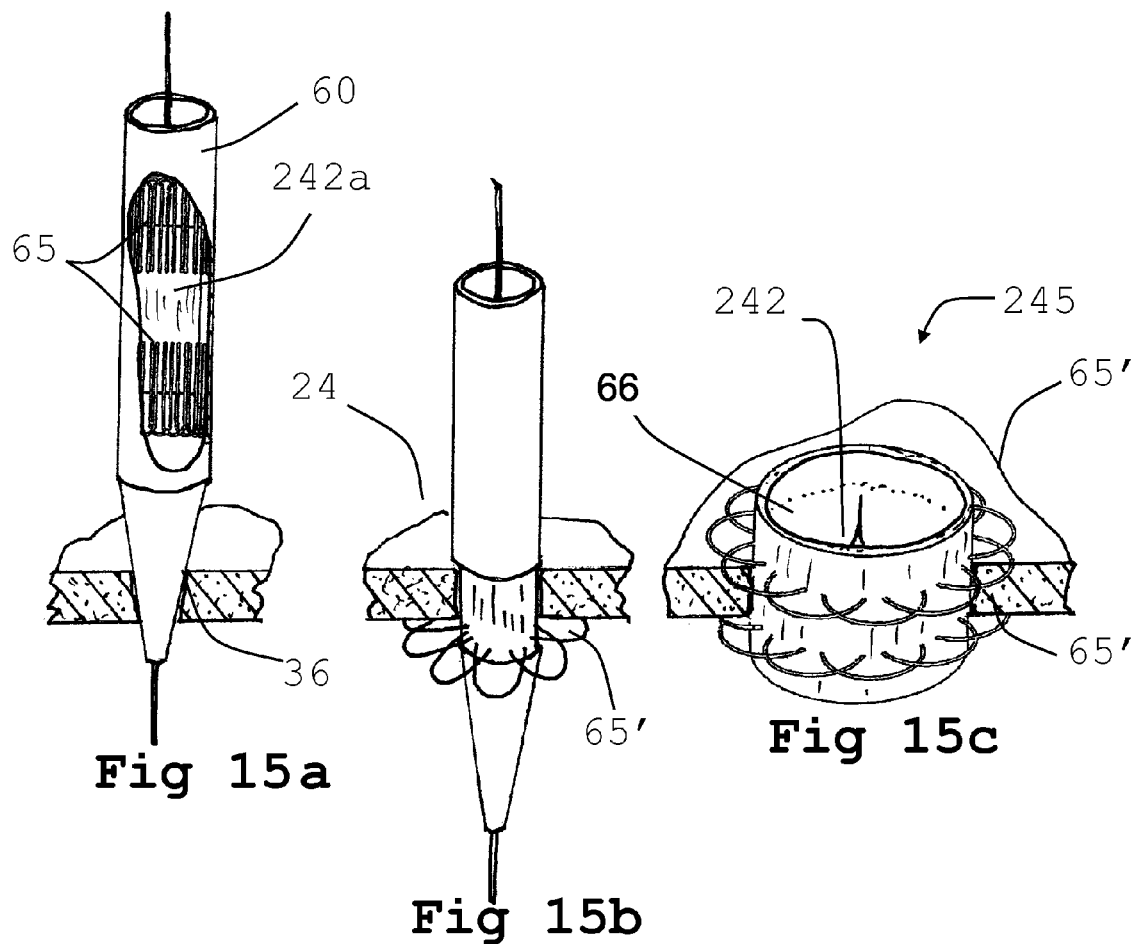

METHOD FOR IMPLANTING PROSTHETIC VALVE

The present invention is a continuation in part of co-pending U.S. patent application Ser. No. 12/803,849, that was filed on 8 Jul. 2010 and is incorporated herein by reference in its entirely. As with the parent application, the present application relates to methods and devices for treating dysfunctional mitral valves, particularly to new medical procedures for installing a prosthetic valve in a new location, but specifically for treating patients who have previously had an "edge to edge" mitral valve repair that may have been performed either by open heart surgery or percutaneously, or for performing together with such an edge to edge procedure.

FIELD OF THE INVENTION

Background of the Invention

Atrioventricular (AV) valves are cardiac valves that prevent backflow from the ventricles into the atria during systole. They are anchored to the wall of the heart at the fibrous skeleton by anchoring tendons named chordae tendineae. The chordae tendineae are attached to papillary muscles. Together, the papillary muscles and the chordae tendineae keep the valves from prolapsing into the atria when they close during systole. The actual opening and closuring of the valves is caused by the pressure gradient across the valve. The left side AV valve is a bicuspid valve having two flaps or leaflets, and is commonly known as the mitral valve due to its shape being reminiscent of a bishop's mitre. The right side AV valve is a tricuspid valve, having three flaps or leaflets. Both of these valves may be damaged and dysfunctional, resulting in leakage during systole, requiring the valves to be repaired or replaced.

A surgical technique known as the edge-to-edge technique was introduced by Alfieri in the early 1990s. This is a simple and effective surgical procedure for the treatment of mitral regurgitation due to complex lesions, for example. The basic concept of this technique is that mitral regurgitation can be corrected simply by suturing the free edge of the diseased leaflet to the corresponding edge of the opposing leaflet exactly where the jet of regurgitated blood is located.

When the jet of regurgitation is in the central part of the mitral valve, the application of the edge-to-edge technique produces a double orifice valve configuration ('double orifice repair') to create a double orifice with improved leaflet coaptation. When the mitral valve lesion is localized in proximity of a commissure, its surgical correction by the edge-to-edge, results in a single orifice mitral valve with a relatively smaller area, in what is known as 'paracommissural repair'.

More recently, a percutaneous method to create a similar type of repair was developed using a trans-septal approach to deliver a clip device that grasps the mitral leaflet edges to create the double orifice. Percutaneous edge-to-edge mitral valve repair can be performed safely and a reduction in MR can be achieved in a significant proportion of patients.

Unfortunately, in many cases, the results of the above discussed procedures are only good for a few months. Many patients require subsequent surgery such as elective mitral valve repair or replacement.

It is an object of the present invention, to provide a method for percutaneously implanting a prosthetic mitral valve apparatus to replace the function of a dysfunctional or diseased mitral valve that has undergone an edge to edge procedure with partial edge to edge stitching or clamping of the valve leaflets.

SUMMARY OF THE INVENTION

The present invention relates generally to the field of medical procedures, and specifically to a method for the implantation of a prosthetic replacement valve apparatus in a novel and non obvious location in a patient's body which neutralized and replaces the function of a native dysfunctional mitral valve that has previously undergone an Alfieri procedure or the like. The replacement causes the full closing of the partially sewn/clamped native valve and thus results in a solution for paravalvular leakage and regurgitation.

In an embodiment of the present invention, a method for the treatment of a patient with a diseased or dysfunctional valve who has previously undergone an Alfieri procedure or a similar edge to edge clamping or sewing procedure to treat regurgitation.

The method comprises the steps of: piercing an aperture through a first leaflet of the edge to edge sewn or clipped valve; advancing and positioning a collapsed prosthetic valve apparatus comprising a one-way valve mounted on an expandable valve seating into the aperture; expanding the expandable valve seating and forcing an outer edge of the first leaflet against a second leaflet, thereby inhibiting the natural separating of the first and second leaflets in diastole by forcing the edges of the leaflets together and preventing their separation, the prosthetic valve providing an alternative passageway for blood pumped whilst inhibiting back-flow in systole.

Optionally, the piercing is by a mechanical tool. Alternatively, the piercing is by a laser tool. Alternatively again, there is no step of piercing and the prosthetic valve is inserted in a natural fissure or tear in the leaflet.

Typically, the first leaflet is an anterior leaflet of the mitral valve.

In one embodiment of the invention the first leaflet of the mitral valve is accessed via the left ventricle and access is by a transvascular approach route, optionally using transcatheterization. Optionally the piercing is performed when the heart is in systole, causing the anterior mitral valve leaflet to coapt with the posterior mitral leaflet.

In another embodiment of the invention, the left ventricle is accessed transapically and the piercing is performed when the heart is in systole, causing the anterior mitral valve leaflet to coapt with the posterior mitral leaflet.

In another embodiment of the invention the right atrium is accessed via the vena cava and the left atrium is accessed by piercing the septum interatrial.

In some embodiments of the invention, the expandable seating is an annular member and the step of expanding the expandable seating comprises inflating a balloon within the annular member.

In other embodiments, the expandable seating comprises a shape-memory super-elastic alloy that expands as it is released from its constraining tube and/or approaches body temperature. Optionally, the shape memory alloy is an alloy of nickel-titanium.

According to some embodiments of the invention, the valve is coated with a material which aids tissue growth.

In some embodiments, the expandable seating has a circumference having a textured surface which engages surrounding tissue to secure the valve apparatus in place.

In one embodiment of the invention, the expandable seating comprises self-expanding shoulders which assist in engaging surrounding leaflet tissue to secure the valve in position.

The method is an effective way or treating a diseased or damaged heart that has previously undergone an Alfieri procedure or a modification thereof, such as percutaneously inserted clip that partially holds the leaflets together in an edge to edge manner. For example, U.S. Pat. No. 8,052,592 to Goldfarb et al, titled "Methods And Devices For Tissue Grasping And Assessment" describes an appropriate clip.

It will be appreciated that the edge-to-edge procedure may be a temporary solution, possibly due to further decay of the heart, stitch absorption, clip displacement, leaflet damage, and the like.

According to some embodiments of the invention, the method comprising a preliminary step of obtaining regulatory approval for the prosthetic valve for insertion into an aperture made within a leaflet of the valve after a previously performed edge-to-edge procedure.

According to some embodiments of the invention, the method comprises a preliminary step of packaging the prosthetic valve apparatus in a package labeled as appropriate for insertion into an aperture made within a leaflet of the valve after a previously performed edge to edge procedure.

According to some embodiments of the invention, the method provides a preliminary step of co-packaging the prosthetic valve apparatus together with instructions describing its suitability for insertion into an aperture made within a leaflet of the valve after a previously performed edge to edge procedure.

According to some embodiments of the invention, the method comprises a preliminary step of marketing the prosthetic valve apparatus for insertion into an aperture made within a leaflet of the valve for correcting a damaged heart previously treated with an edge to edge procedure.

The weight of the prosthetic embedded in a heart valve leaflet may risk the leaflet to collapse into the ventricle. This risk may be eliminated if the leaflets are sutured or clipped together, edge to edge in an Alfieri type procedure.

Thus according to some embodiments of the invention, the method comprising a preliminary step of obtaining regulatory approval for the prosthetic valve for insertion into an aperture made within a leaflet of the valve at the same time as performing edge-to-edge procedure, i.e. during the same 'surgical operation'.

According to some embodiments of the invention, the method comprises a preliminary step of packaging the prosthetic valve apparatus in a package labeled as appropriate for insertion into an aperture made within a leaflet of the valve together with performing an edge to edge procedure.

According to some embodiments of the invention, the method provides a preliminary step of co-packaging the prosthetic valve apparatus together with instructions describing its suitability for insertion into an aperture made within a leaflet of the valve together with performing an edge to edge procedure.

According to some embodiments of the invention, the method comprises a preliminary step of marketing the prosthetic valve apparatus for insertion into an aperture made within a leaflet of the valve for correcting a damaged heart previously treated with an Alfieri type procedure.

BRIEF DESCRIPTION OF THE DRAWINGS

The foregoing and other features of the present invention will become apparent to those skilled in the art to which the present invention relates upon reading the following description with reference to the accompanying drawings, in which:

FIGS. 15a-c depict a perspective view of a self expandable valve with self expandable shoulders which assist in securing the valve in its proper position, according to another embodiment of the present invention;

Figure 1:
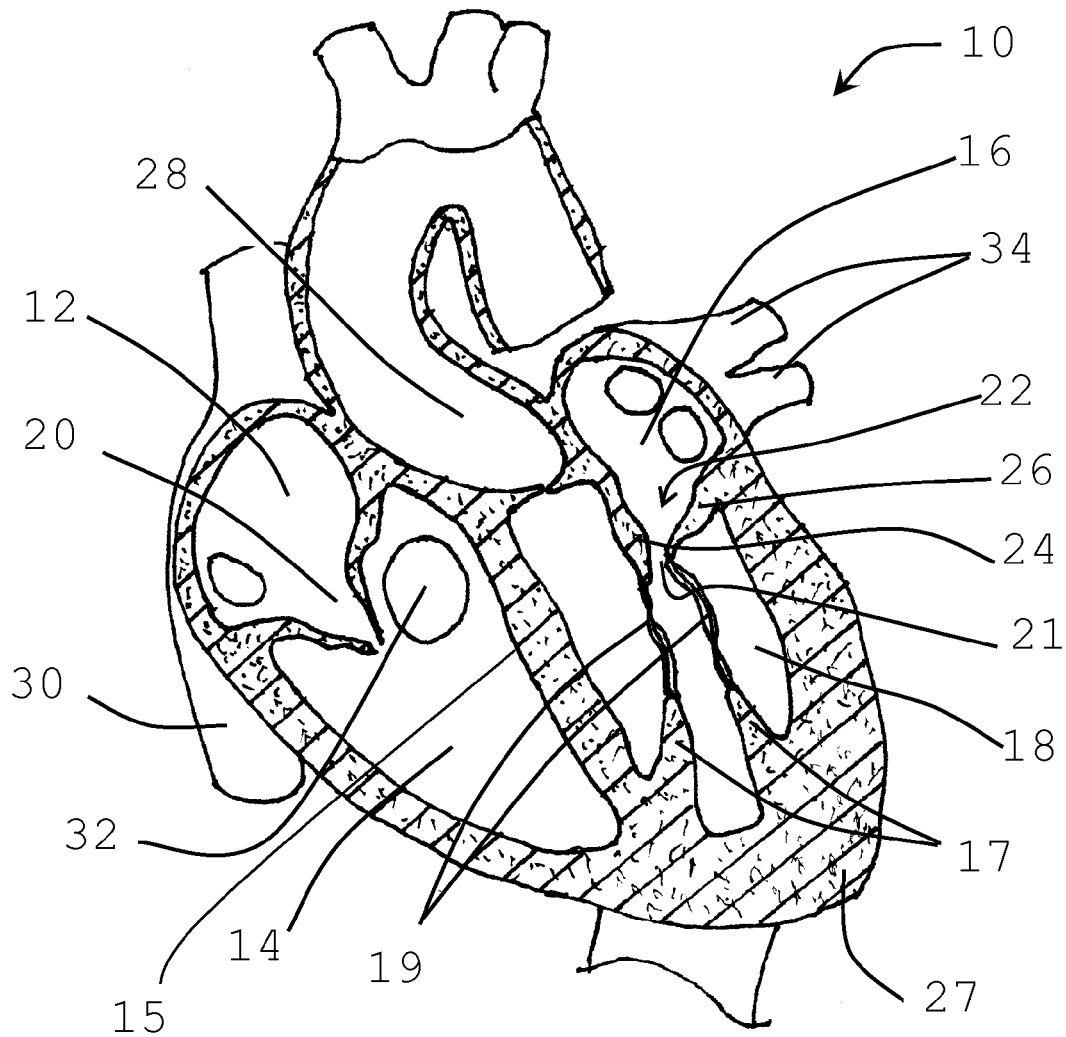
FIG. 1 is a vertical section through a heart.

For clarity, method steps are annotated with letters and the illustrative Figures with numbers. The same numbering scheme is used consistently where appropriate to aid clarity.

DETAILED DESCRIPTION OF THE EMBODIMENTS

The present invention relates to a method for implanting a prosthetic valve apparatus in a novel and unexpected location. In this manner, the function of a prosthetic mitral valve is provided by the prosthetic valve and the native dysfunctional valve is voided, thereby avoiding paravalvular leakage. The method takes advantage of the special structural features of the tissue of the native leaflets and annulus of the mitral valve to keep the valve secured in place. The anterior leaflet extends across the annulus, which is an area of heart wall tissue at the junction of the atrial and ventricular walls that is relatively fibrous and significantly stronger than leaflet tissue. It provides structural support for the prosthetic valve and prevents its detachment from the novel orifice. It will be noted that the free edge of the valve leaflet has a reinforced, sinewy structure that is significantly stronger than central portions of the leaflet.

The method may be deployed after an Alfieri procedure, that sutures the mitral leaflets together edge to edge, or after an equivalent percutaneous procedure such as a clip for holding the valve leaflets together edge to edge, such as that described in U.S. Pat. No. 8,052,592 to Goldfarb et al, for example.

Thus embodiments of the present invention may correct, improve or replace an edge to edge procedure. Furthermore, the edge to edge procedure may improve the procedure described in the parent application in that the edge to edge attachment prevents the leaflet and valve collapsing and falling into the left ventricle.

It will be noted that different known prosthetic valve apparatuses may be used with embodiments of the present invention. For example a particular valve prosthesis of the type depicted in U.S. Pat. No. 7,618,446 to Andersen et al. titled "Valve prosthesis for implantation in the body and a catheter for implanting such valve prosthesis" or that described in U.S. Pat. No. 7,611,534 to Kapadia, et al titled "Percutaneous atrioventricular valve and method of use" may be used with the presently disclosed method, rendering it more cost effective and easy to use.

It will be appreciated that implantation of a prior-art prosthetic in the manner intended by the manufacturers, i.e. in series with the natural valve, results in a given prosthetic being suitable for insertion in a very specific size and type of heart and requires the manufacturing of and availability of a whole selection of prosthetics to treat a population of patients. In contradistinction, in the new methodology described herein, the same prosthetic could be used for repairing a heart, irrespective of the size, age or gender of the patient. Hence this method enables enhanced tolerance to sizing as there is no need to specify a mitral valve that is accurately sized for the left atrium of a specific patient, and to create or select an appropriately-sized replacement apparatus. Essentially sizing need only take into account the functionality and proper blood flow, with the valve being big enough to enable proper sealing, but not being too big to risk aortic valve dysfunction. It will thus be appreciated that relatively few prosthetics having different sizes and shapes will be sufficient to treat the vast majority of cases.

With reference to FIG. 1, a vertical section through a heart is shown. The heart 10 consists of a right atrium 12, a right ventricle 14, a left atrium 16 and a left ventricle 18. The right and left atria 12, 16 are separated by the septum interatrial 15. The right atrium 12 and right ventricle 14 are separated by a tricuspid valve 20, and the left atrium 16 and left ventricle 18 are separated by a bicuspid valve, also known as the mitral valve 22 that consists of an anterior leaflet 24 and a posterior leaflet 26 having edges that separate and come together as the left ventricle 18 dilates and contracts to force blood into the aorta 28. Deoxygenated blood from the body flows through the vena cava 30 into the right atrium 12 and is sucked into the right ventricle 14 through the tricuspid valve 20 as it dilates. The right ventricle 14 pumps the blood via the pulmonary artery 32 to the lungs. Oxygenated blood from the lungs flows via the pulmonary veins 34 into the left atrium 16 and is sucked into the left ventricle 18 via the orifice between the edges of the leaflets 24, 26 of the mitral valve 22. Systole of the heart 10 pumps the oxygenated blood through the aorta 28 and around the body. The anterior and posterior leaflets 24, 26 of the mitral valve 22 flex together as the left ventricle 18 contracts, to prevent blood being pushed back to the left atrium 16. Papillary muscles 17, chordae tendineae 19 and the heart apex 27 are also shown. The mitral valve 22 undergoes tremendous strain and the present invention is directed to novel methods of treating a patient with a dysfunctional or diseased mitral valve 22.

Figure 4:
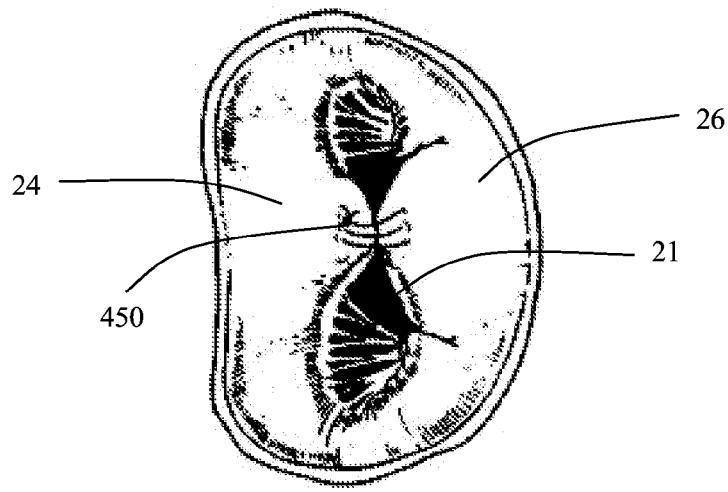
FIG. 4 shows a diseased mitral valve where an edge-to-edge technique has been used as a double orifice repair.
Figure 5:
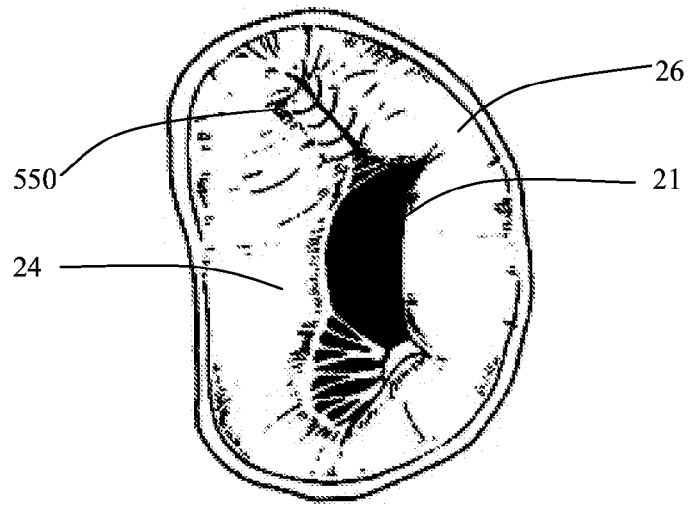
FIG. 5 shows a diseased mitral valve where an edge-to-edge technique has been used as a paracommissural repair.

Prior art surgical treatment of dysfunctional mitral valves 22 involves either repairing the valve 22, and/or adding a prosthetic one-way valve in series with the mitral valve 22 to perform the same functionality, or inserting a prosthetic one-way valve between the leaflets 24, 26 of the native orifice 21 of the mitral valve 22. A further prior art treatment discussed below with reference to FIGS. 4 and 5, is the edge to edge treatment, where mating edges of the anterior and posterior mitral valves are partially sutured or clipped together where mitral regurgitation occurs.

Figure 2A:
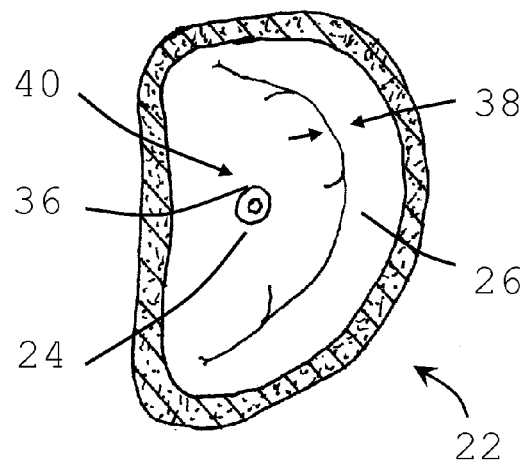
FIGS. 2a and 2b are schematic top views of mitral valve leaflets, with prosthetic valve apparatus implanted in anterior leaflet in collapsed and expanded configuration.

With reference to FIG. 2a, in contradistinction to the prior techniques, in the present invention, the dysfunctional or diseased mitral valve 22 is treated by creating a hole 36 in one of the leaflets, typically the anterior leaflet 24, inserting a prosthetic valve 40 in a collapsed state, and expanding the prosthetic valve to its expanded state 40', thereby wedging it into the hole 36, and widening the hole 36 into an orifice 36'. This novel approach of creating an additional orifice 36' and voiding the existing orifice 21 between the edges 38 of the leaflets 24, 26 is counter-intuitive and teaches away from the prior art. The method is advantageous since it avoids damaging chordea tendineae 19 and papillary muscles 17.

Figure 2B:
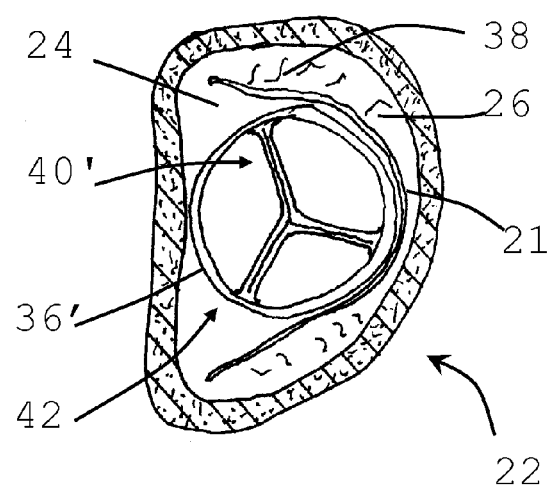

Thus with reference to FIG. 2a, a hole 36 is created in the mitral valve 22 by piercing the anterior mitral leaflet 24 away from the mating edges 38 of the leaflets 24, 26 and preferably near the center of the anterior leaflet 24. An expandable prosthetic valve 40 is introduced into the hole 36 in its collapsed state as shown in FIG. 2a and expanded therein to assume an expanded configuration 40' shown in FIG. 2b, wedging the expandable seating 42 of the prosthetic 40' into the hole 36, now an orifice 36', and forcing the edges 38 of the leaflets 24, 26 together, thereby closing and voiding the native orifice 21 of the valve 22.

Figures 3A, 3B:
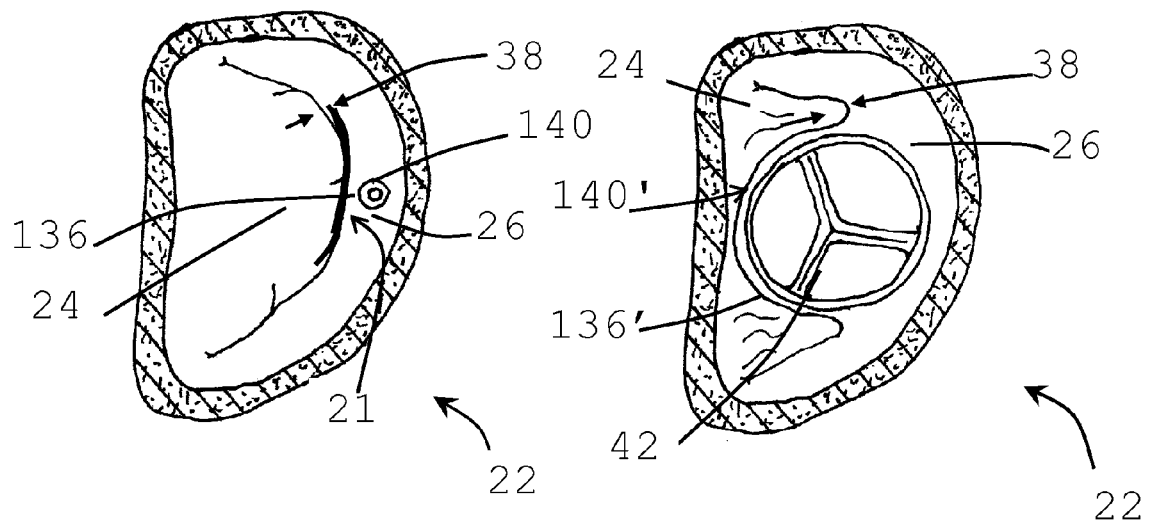
FIGS. 3a and 3b are schematic top views of mitral valve leaflets, with prosthetic valve apparatus implanted in posterior leaflet in collapsed and expanded configuration, respectively.

With reference to FIGS. 3a and 3b, in cases where the condition of the patient does not enable piercing of the anterior leaflet 24 or in different anatomical conditions where the shape of the leaflets 24, 26 and/or the native orifice 21 is in a different orientation to the normal state it is also possible to make the hole 136 in the posterior leaflet 26, to insert a prosthetic 140 whilst in its collapsed state, and to expand it into an expanded state 140' in situ, widening the hole 136 into an aperture 136', mutatis mutandis. Similarly, where a hole or tear pre-exists in one of the leaflets 24, 26 for whatever reason, the prosthetic 40 (140) may be inserted thereinto. The hole 36 (136) perforates all layers of the leaflet. i.e. the *atrialis*, *fibrosa* and *spongiosa*. Piercing is preferably performed when the heart 10 is in systole causing the edges 38 of the anterior and posterior mitral valve leaflets 24, 26 to coapt. It will be noted that the internal structure of the leaflets 26, 24 towards their edges 38 is fibrous and tough and the present invention avoids damaging this structure.

FIG. 4 shows a diseased mitral valve where an edge-to-edge technique has been used as a double orifice repair. The mating edges of the anterior 24 and posterior 26 leaflets are sutured together with sutures 450 at the position where there is a jet of mitral regurgitation.

FIG. 5 shows a variant procedure where a diseased mitral valve where an edge-to-edge technique has been used as a paracommissural repair, stitching the leaflets together at one edge of the valve with sutures 550 effectively shortening the opening between the leaflets 24, 26.

Figure 6:
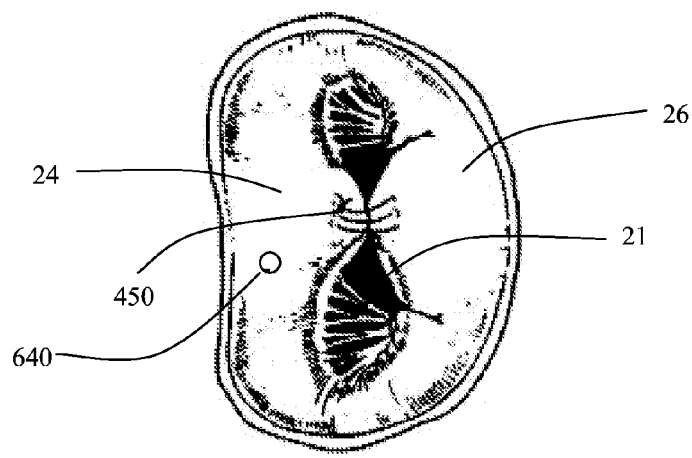
FIG. 6 shows the diseased mitral valve of FIG. 4 with a generalized prosthetic valve implanted in an incision in a leaflet prior to expanding the valve to wedge it in place and to force the edges of the leaflets together, essentially canceling the native valve.

FIG. 6 shows a diseased mitral valve where an edge-to-edge technique has been used as a double orifice repair as in FIG. 4, mutatis mutantis, but where an incision has been made in a leaflet (here the anterior leaflet 24) and an expandable prosthetic valve 640 has been inserted into the incision. On expansion, the prosthetic valve 640 forces the edges of the valves together, closing the native orifice 21 and providing an alternative orifice for blood flow. It will be noted that the edge to edge sutures 450 may prevent the leaflet 24 and valve 640 from falling backwards into the chamber and causing heart failure.

This new surgical procedure of installing a prosthetic valve 640 within a leaflet 24 of a mitral valve provides a solution to a number of cardiac problems relating to the mitral valve 22 such as leaflet displacement, regurgitation and dilation, and may be applied to correct an Alfieri procedure or to treat further deterioration after a successful Alfieri procedure. It will be noted that there is generally no need for positioning an annuloplasty ring, or for prior sizing. This method is thus both cost-effective and is suitable for a wide population. It also avoids rupture of the chordae tendeae (19 in FIG. 1). Although FIG. 6 shows the prosthetic valve 640 inserted into an aperture or incision in the anterior leaflet 24, it will be appreciated that the prosthetic valve 640 may alternatively be inserted into an aperture or incision in the posterior leaflet 24, where deemed appropriate.

Figure 7:
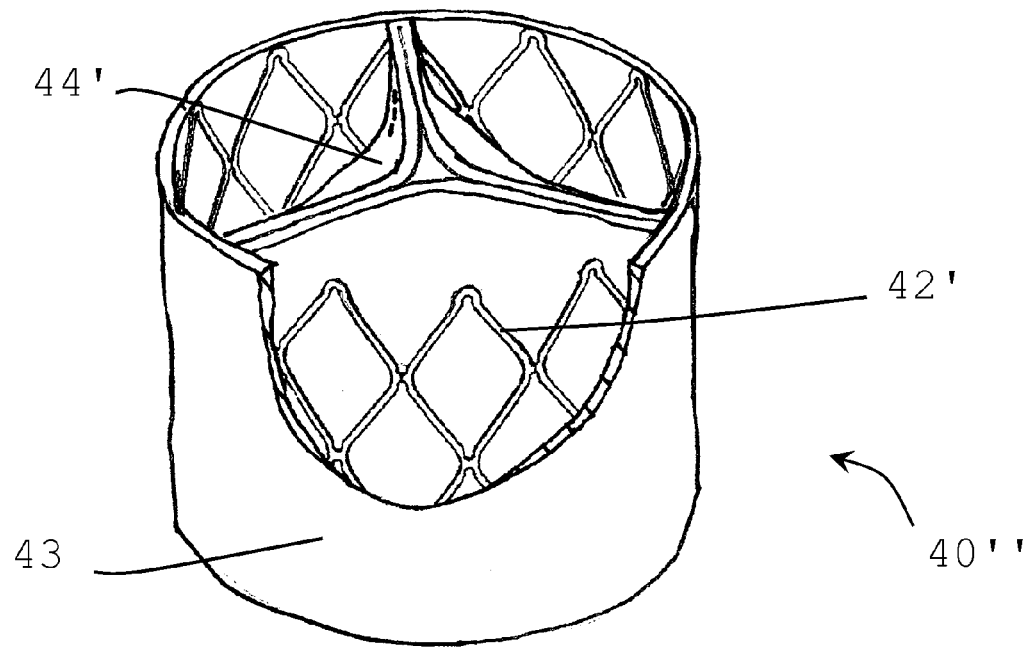
FIG. 7 shows a generalized prosthetic valve.

With reference to FIG. 7, a generalized prosthetic valve 40" is shown. Prosthetic valve 40" consists of an expandable valve seating 42' coupled to a one-way valve 44'. The expandable valve seating 42' may be covered with a fabric cover 43 which serves to prevent paravalvular leak and aids tissue growth.

It will be appreciated that the novel approach presented herein may be used with a range of expandable prosthetic valves, including valves that are currently available but were designed for insertion into the opening between the leaflets 24, 26 of the natural mitral valve 22.

Figure 8:
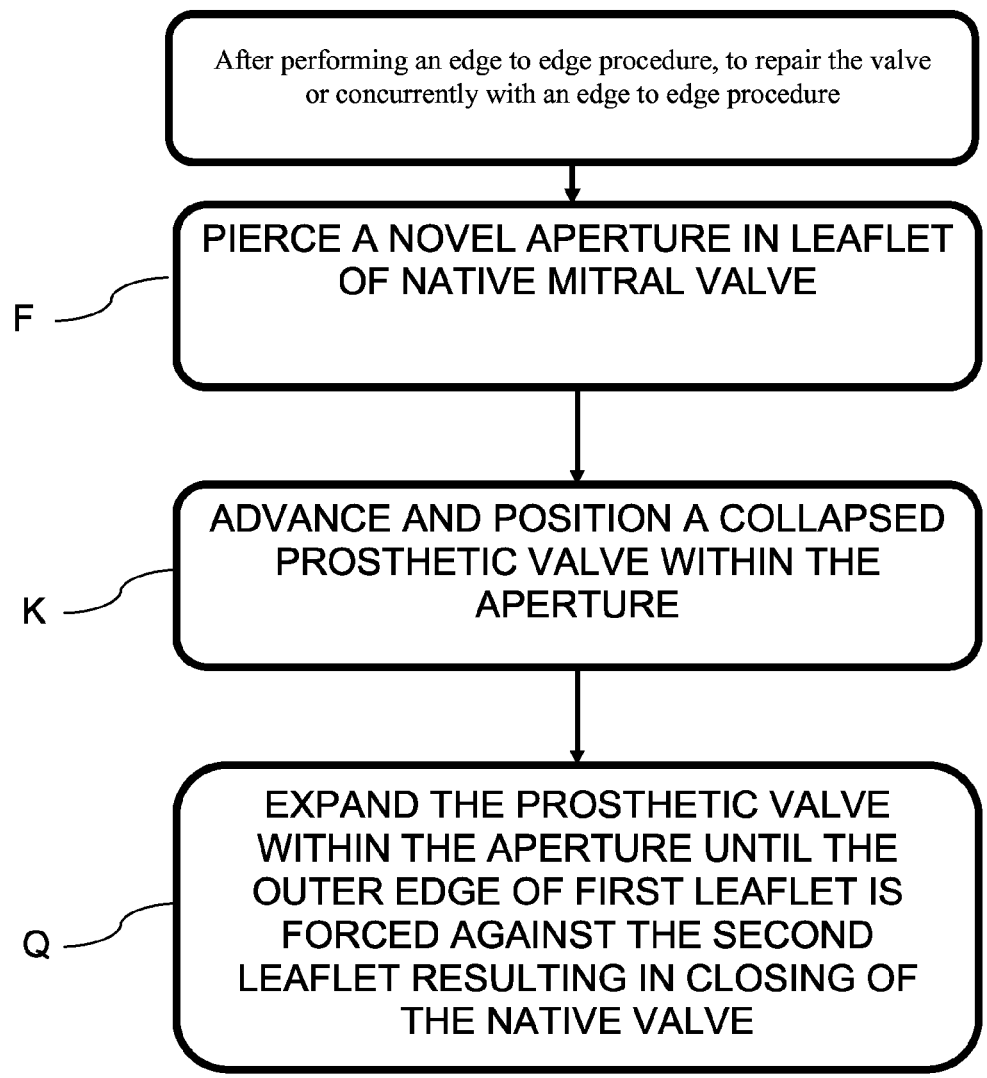
FIG. 8 is a flow chart describing generically, the essential steps of the method of the invention.

With reference to FIG. 8, a flowchart illustrating the main stages of a method for implanting a prosthetic valve 40 in accordance with the invention is shown. To repair a damaged valve after previously performing an edge to edge procedure, or concurrently with the edge to edge procedure in the same 'operation', a hole 36 is created in a leaflet 24 (26) of the native mitral valve 22—Step F. The piercing of the hole 36 may be performed with a mechanical tool such as a needle, hot wire or guide-wire. Alternatively a laser tool may be used. Various access routes including transvascular and transapical approaches are described below in FIGS. 9 to 11. The expandable seating 42 of a prosthetic valve 40 is positioned in the hole 36—Step K, and the expandable seating 42 is expanded—Step Q thereby opening the hole 36 into an aperture 36' and wedgingly locking the seating 42 within the aperture 36'. The expansion may be effected using an expansion arrangement comprising a balloon 70—(FIG. 14) inserted to the valve site via an introducing sheath 49 (FIG. 9) or catheter 50 (FIG. 10), or the valve seating 42 itself can be self-expanding, perhaps being fabricated from a shape memory alloy that may be introduced at a low temperature, and which undergoes a phase transformation as it warms to body temperature. The prosthetic valve may be alternatively fabricated from super-elastic material, so that is it is inserted into the hole 36 whilst constrained in an over-tube 60 (FIG. 15), and then expanded to a larger working diameter when released from the over-tube 60. As the valve 40 expands, it widens the hole 36 into an aperture 36' and forces the outer edge of the first, pierced leaflet against the second leaflet, thereby cancelling or at least minimizing the natural orifice 21 and closing of the leaflets 24, 26 by forcing the edges 38 (FIG. 2, FIG. 3) of the leaflets 24, 26 together and preventing their separation. Whilst voiding the native mitral valve 22, the prosthetic valve 40' wedged into the aperture 36 provides an alternative passageway for blood pumped from the left atrium 16 to the left ventricle 18 on dilation of the left ventricle 18 whilst inhibiting back-flow in systole and the expanded prosthetic valve 40' becomes operational so that the patient has cardiac output.

Figure 9:
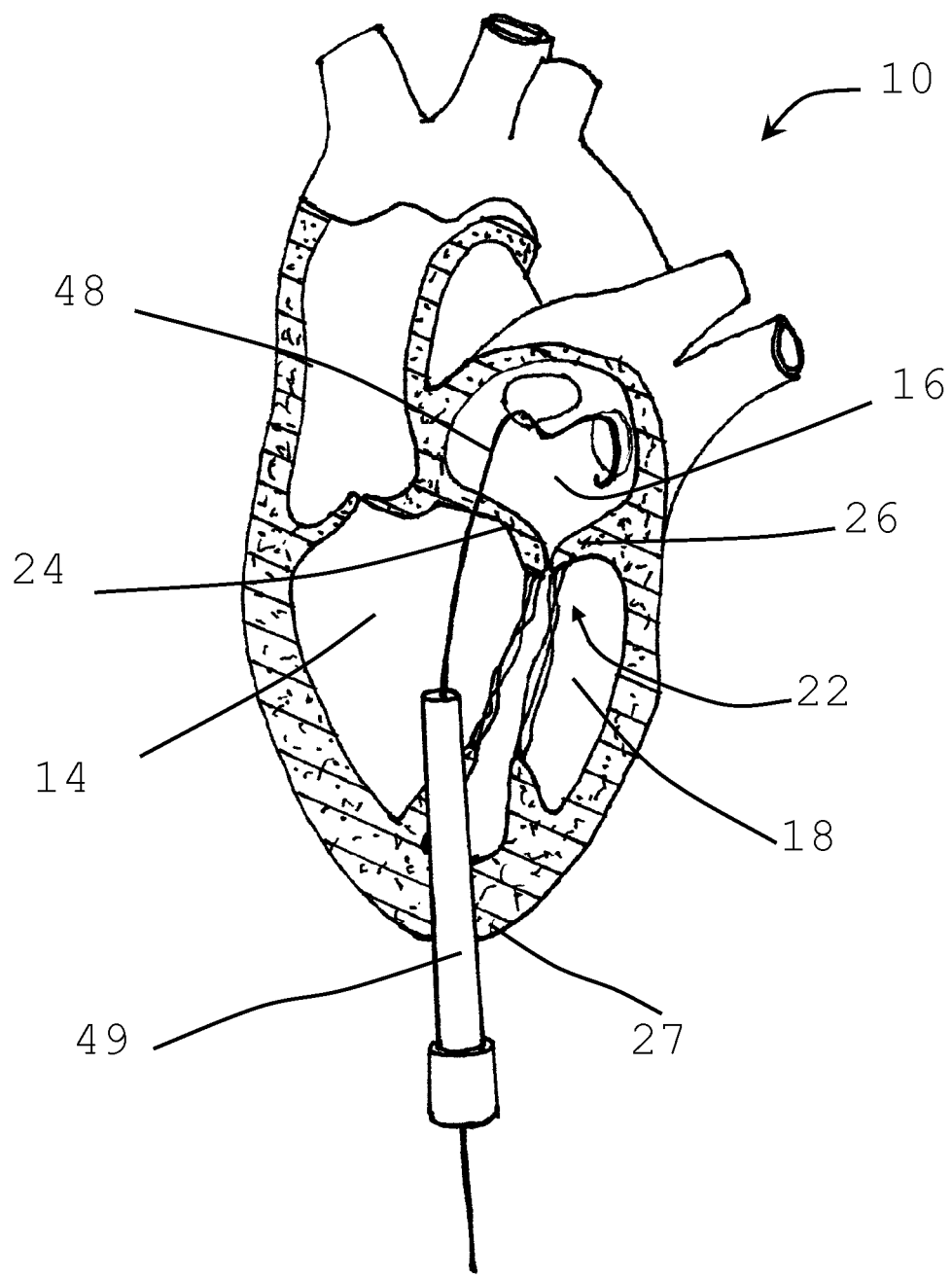
FIG. 9 represents schematically a transapical approach to implant heart valves, according to one embodiment of the present invention.

Access to the mitral valve 22 may be via the left atrium 16 or via the left ventricle 18, and there are a number of possible percutaneous routes. With reference to FIG. 9, access to the valve 22 may be transapically i.e. via the heart apex 27, typically piercing the anterior leaflet 24 when the heart 10 is in systole causing the anterior mitral valve leaflet 24 to coapt with the posterior mitral leaflet 26. Alternatively, as shown in FIGS. 7 and 8, access via the left ventricle 18 may be by a transvascular approach route, typically using transcatheterization.

Figure 10:
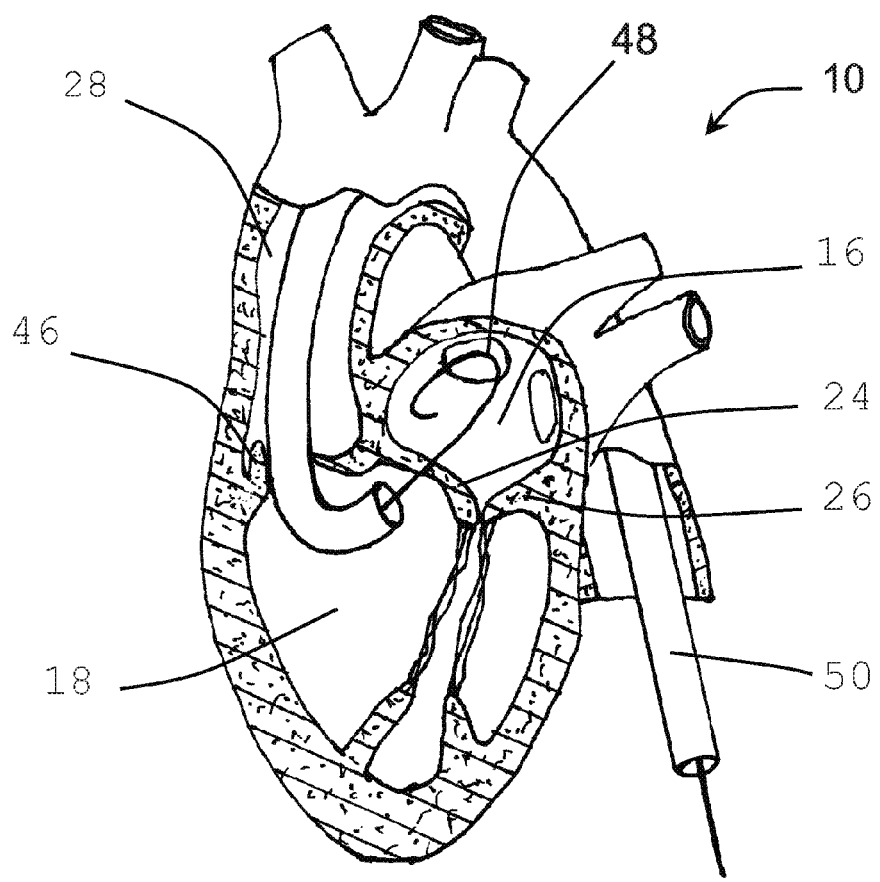
FIGS. 10 and 11 represent schematically different possible transcatheter approaches to implant heart valves, according to other embodiments of the present invention.
Figure 11:
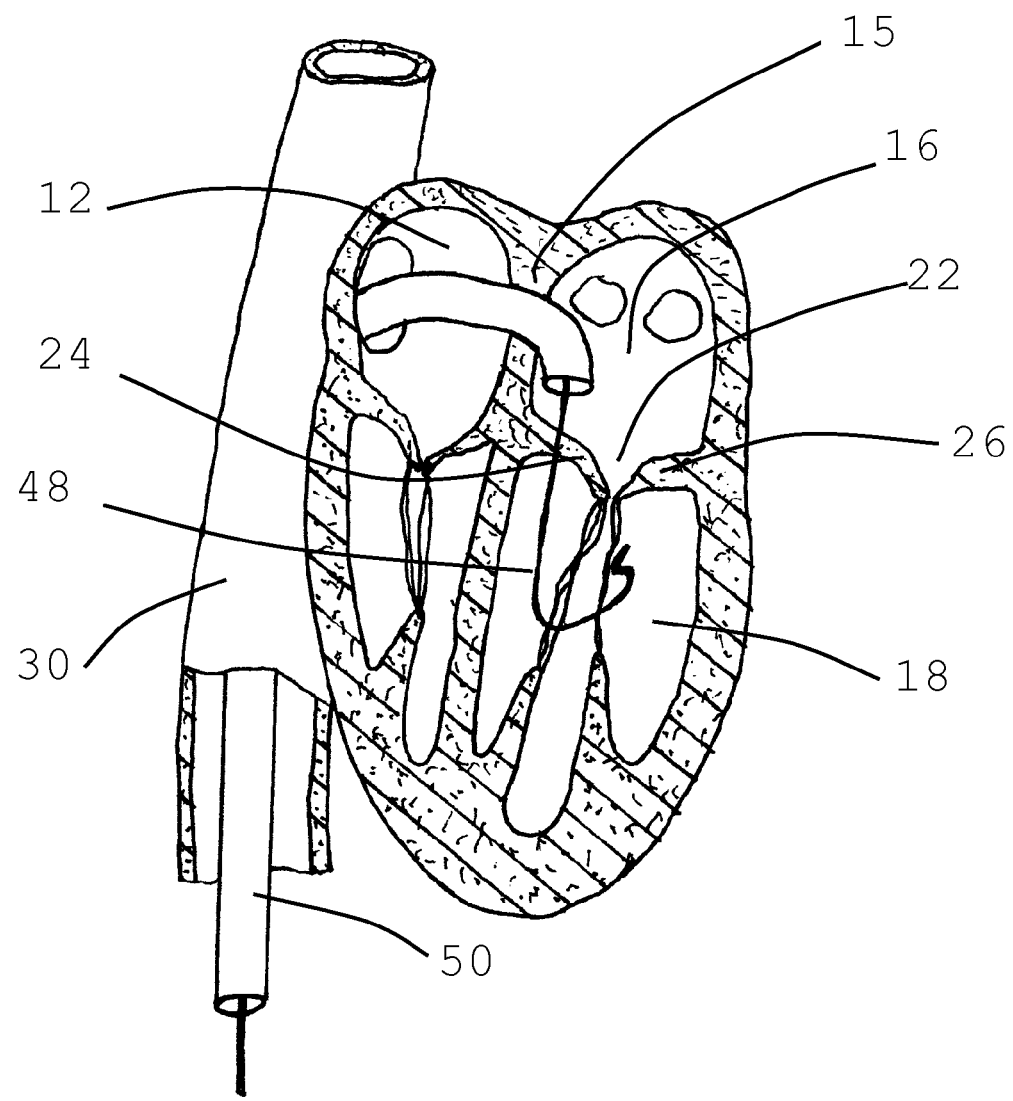

In FIG. 10, in a variant method, access to the anterior mitral valve leaflet 24 is via the left ventricle 18 with access to the ventricle 18 via the aorta 28 and aortic valve 46. Unlike the parent application, there is generally no strong preference for the piercing to be performed when the heart 10 is in systole causing the anterior mitral valve leaflet 24 to coapt with the posterior mitral leaflet 26, since the edge to edge sutures or clip holds at least part of the valve closed.

Alternatively, as shown in FIG. 10, the anterior leaflet 24 of the mitral valve 22 is accessed via the right atrium 12 by a transvascular approach, typically using transcatheterization, with the right atrium 12 being accessed via the vena cava 30 and the left atrium 16 is accessed by piercing septum interatrial 15.

It will however be appreciated that this novel positioning and usage of a prosthetic valve 40 may be by open heart surgery.

Figure 12A:
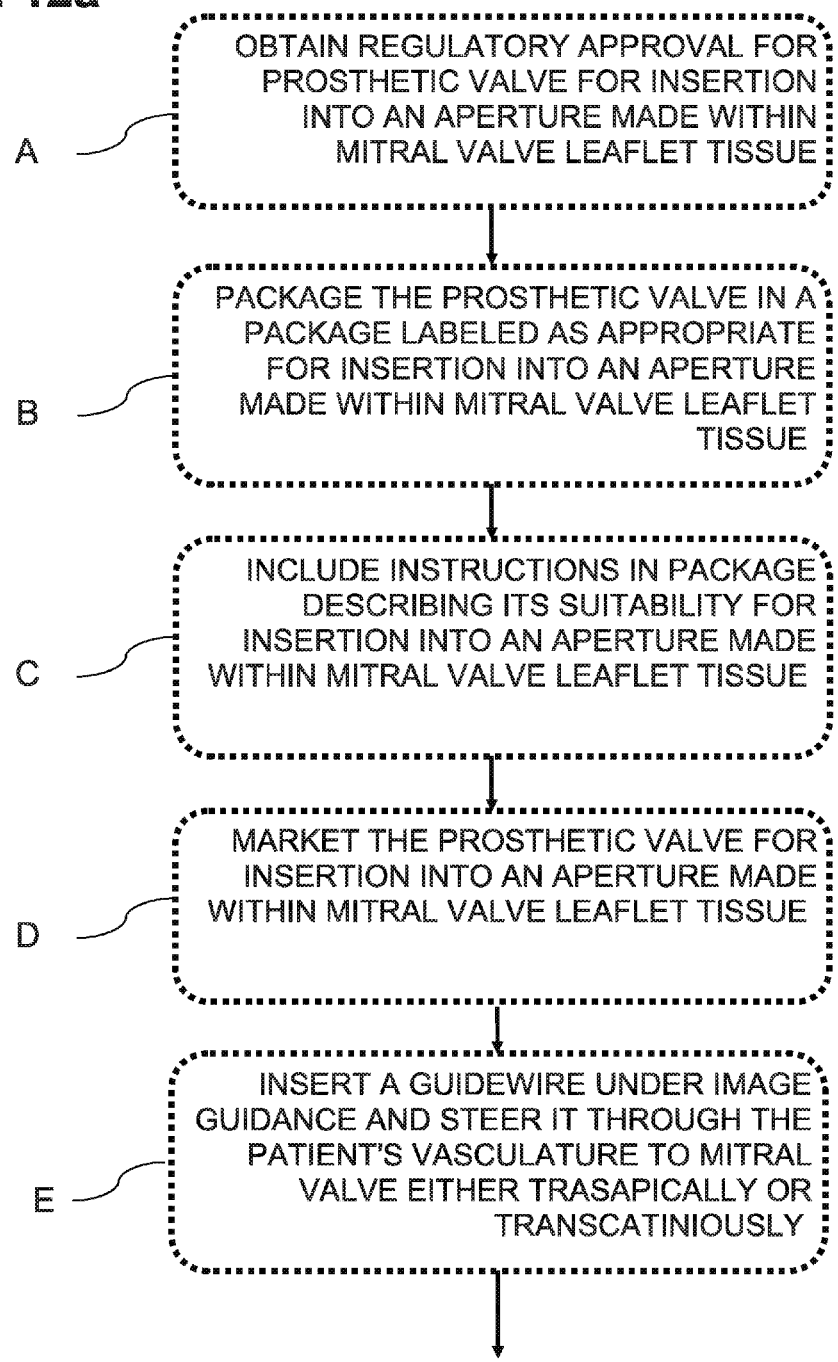
FIGS. 12(a-c) depict a flow chart showing the steps of implanting and securing a mitral prosthetic valve apparatus within a novel location, which allows it to replace the functionality of a dysfunctional valve, according to a detailed embodiment of the present invention.
Figure 12B:
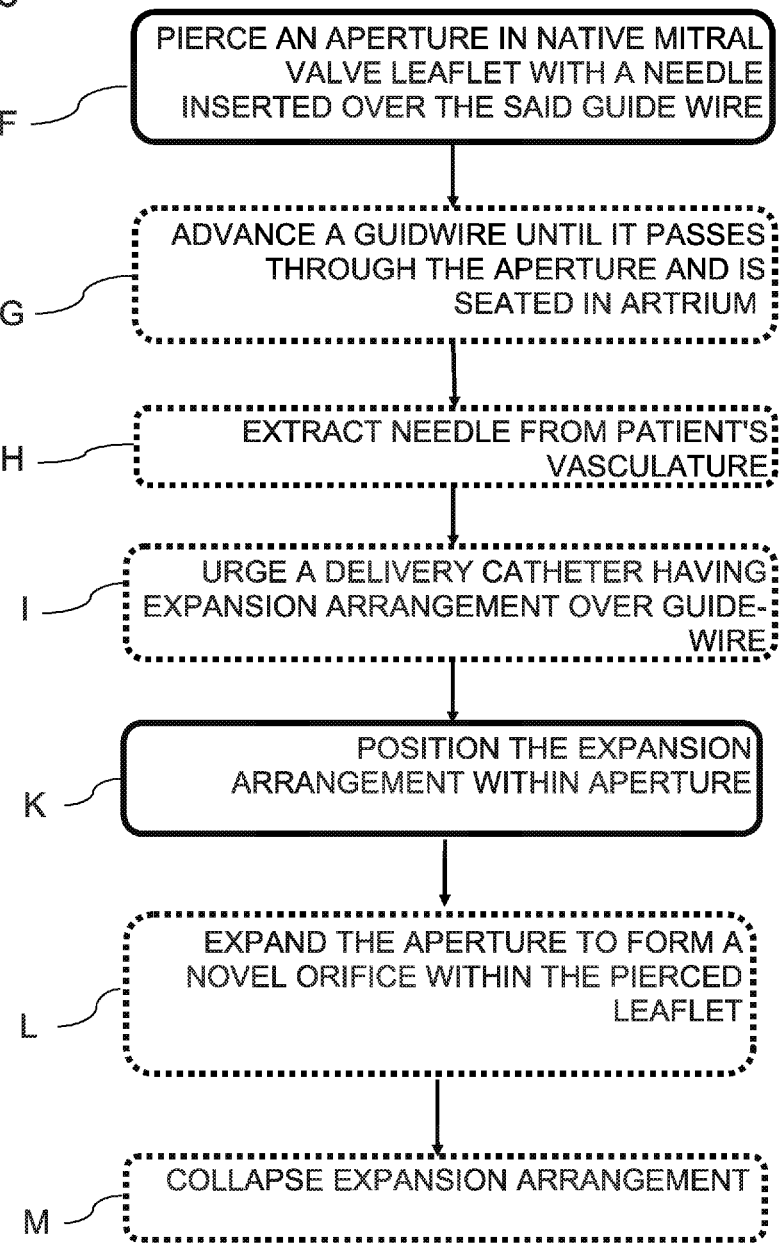

With reference to FIGS. 12(*a-c*), a more detailed process is provided. Preferably in addition to the edge to edge suturing or clipping by an Alfieri procedure or variation thereof, which may be performed immediately before positioning the prosthetic heart valve or concurrently therewith, or immediately afterwards, but typically is performed some months earlier, one or more additional preliminary steps are performed prior to surgery. These may include obtaining regulatory approval for a new, variant of pre-existing prosthetic valve 40 for use with the methodology described hereinabove—Step A. Another useful preliminary step is to package the prosthetic valve 40 in a package (not shown) labeled as appropriate for insertion into an aperture or hole 36 made within the tissue of a leaflet 24 (26) of a mitral valve 22—Step B, and/or including instructions (not shown) for the novel operation as described herein within the package of the prosthetic valve 40—step C. Another preliminary step is marketing the prosthetic valve 40 for insertion into an aperture 36 made within the tissue of a leaflet 24 (26) of a mitral valve 22—Step D.

Figure 13A:
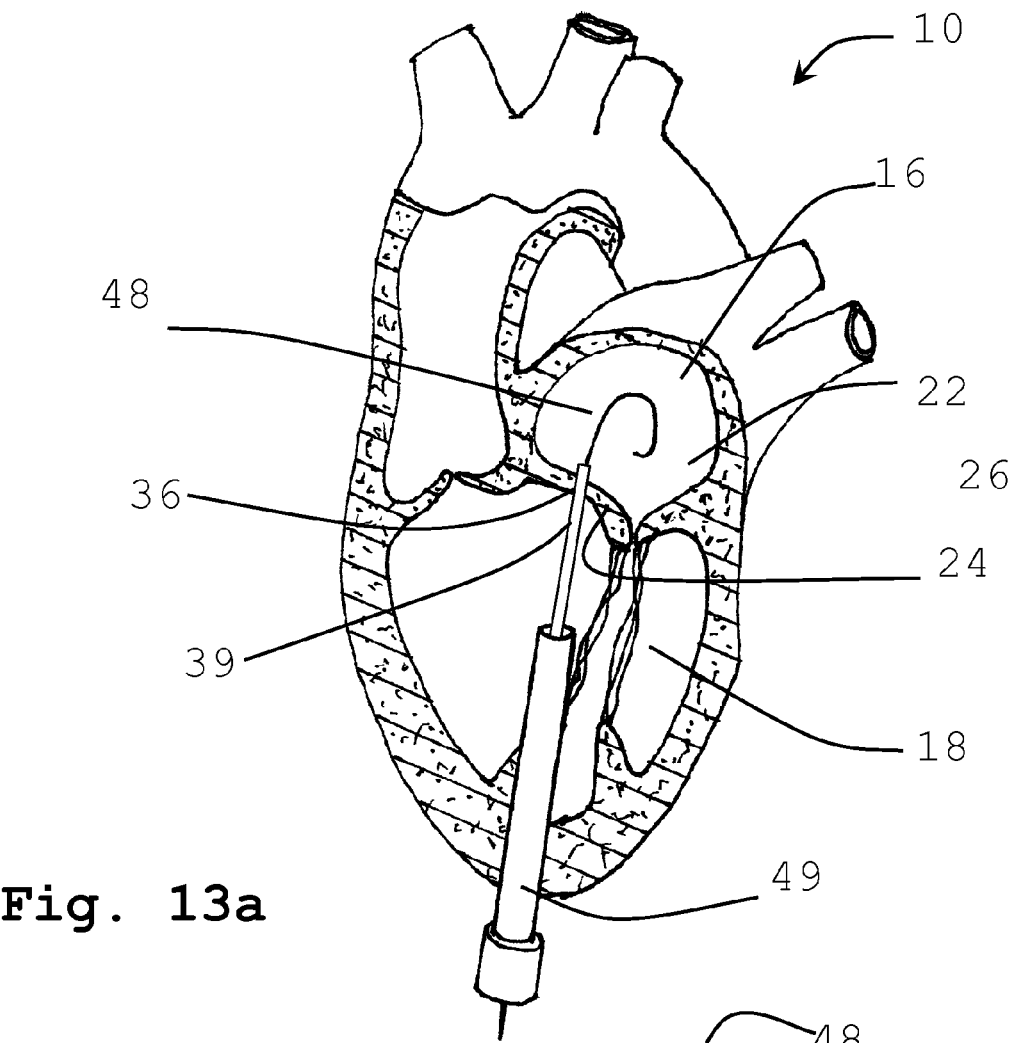
FIGS. 13a-j represent schematically, the steps of implanting and securing a mitral prosthetic valve apparatus within a novel location, which allows it to replace the functionality of a dysfunctional valve, according to an embodiment of the present invention.
Figure 13B:
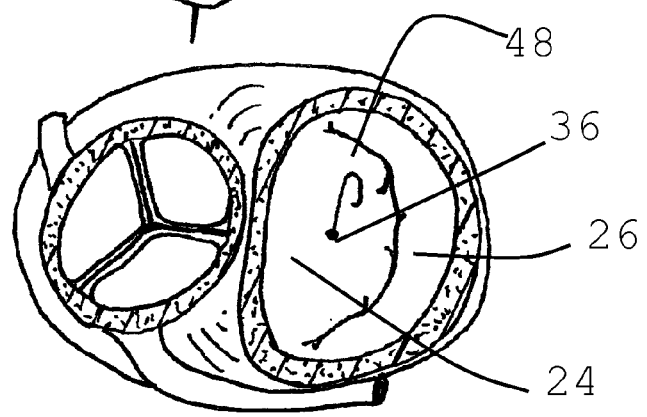

Thus (unless, open heart surgery is used), a mechanical tool such as a needle 39 (FIG. 13*a*) is typically inserted under image guidance and steered through the patient's vasculature either transapically via a sheath 49 (FIG. 13*a*) or transcutinaously via guiding catheter 50 (FIGS. 10 and 11) to mitral valve 22—step E. A first leaflet 24 (or 26) is pierced, at or near its center—step F, typically using a needle a guide wire, a laser tool, or perhaps a mechanical tool such as a scalpel or hot wire, to create a novel hole or aperture 36 (FIG. 13*a*). This may be performed when the leaflet is stretched during systole or the rim of the leaflet to be pierced being held with a tool such as a forceps or suture holder. Next a guide-wire 48 (FIG. 13*a*) may be advanced in the same manner until it passes through the aperture 36 (FIG. 13*a*), into the left atrium 16—step G and the needle, etc. 39 (FIG. 13*a*) is extracted from patient's vasculature—step H. Such a guide-wire 48 (FIG. 13*a*) will usefully have a very soft distal tip to protect the left atrium 16 which has a very delicate and thin myocardium.

Figure 13C:
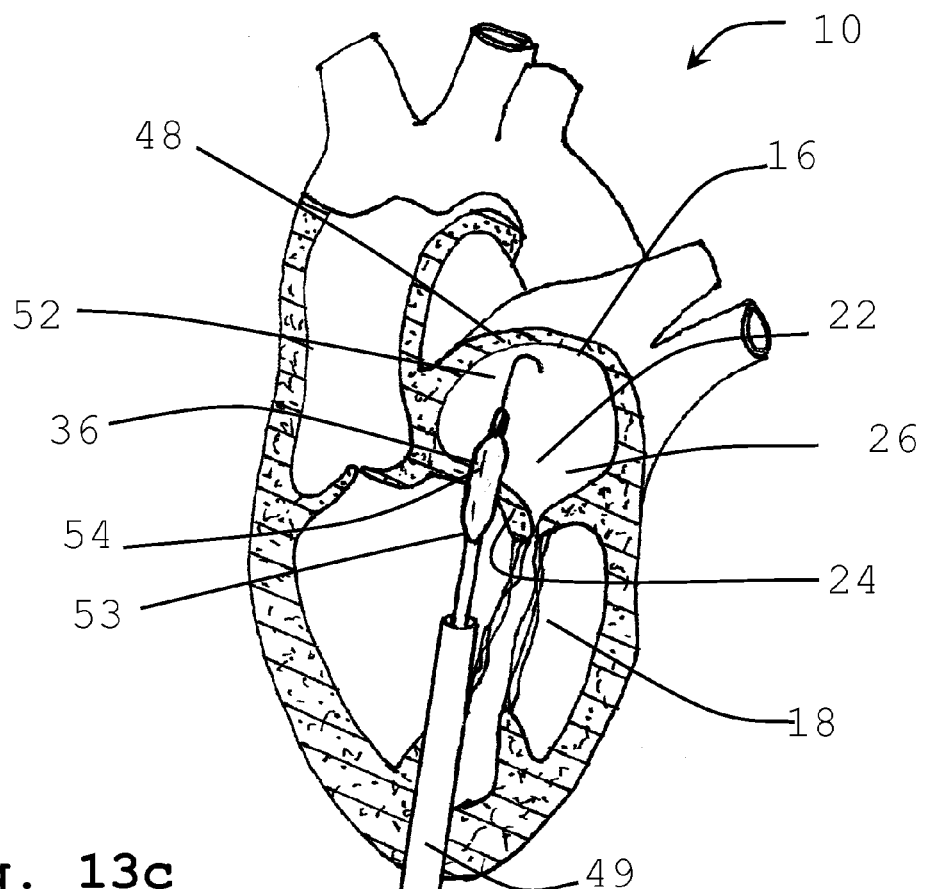
Figure 13D:
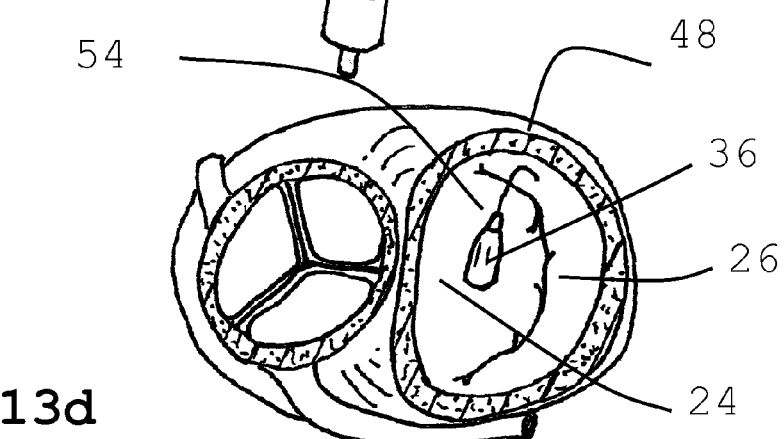

A catheter, having an expansion arrangement, typically a balloon catheter 53 (FIG. 13*c*) I then urged through the sheath 49 and over the guide wire 48—step I. the expansion arrangement, in this figure, 10*c* an inflatable balloon 54 at the distal end of the catheter 53 is positioned in the aperture 36—Step K, aperture can be expanded—Step L to form a novel orifice 36' within the pierced anterior leaflet 24 (FIG. 13*c*, 13*d*), possibly by inflating a balloon 54 (FIG. 13*c* 13*d*). Next, the expansion arrangement of the catheter is collapsed—Step M, possibly by deflating the balloon 54 (FIG. 13*c*) and the catheter 53 (FIG. 13*c*) is extracted—Step N.

Figures 13E, 13F:
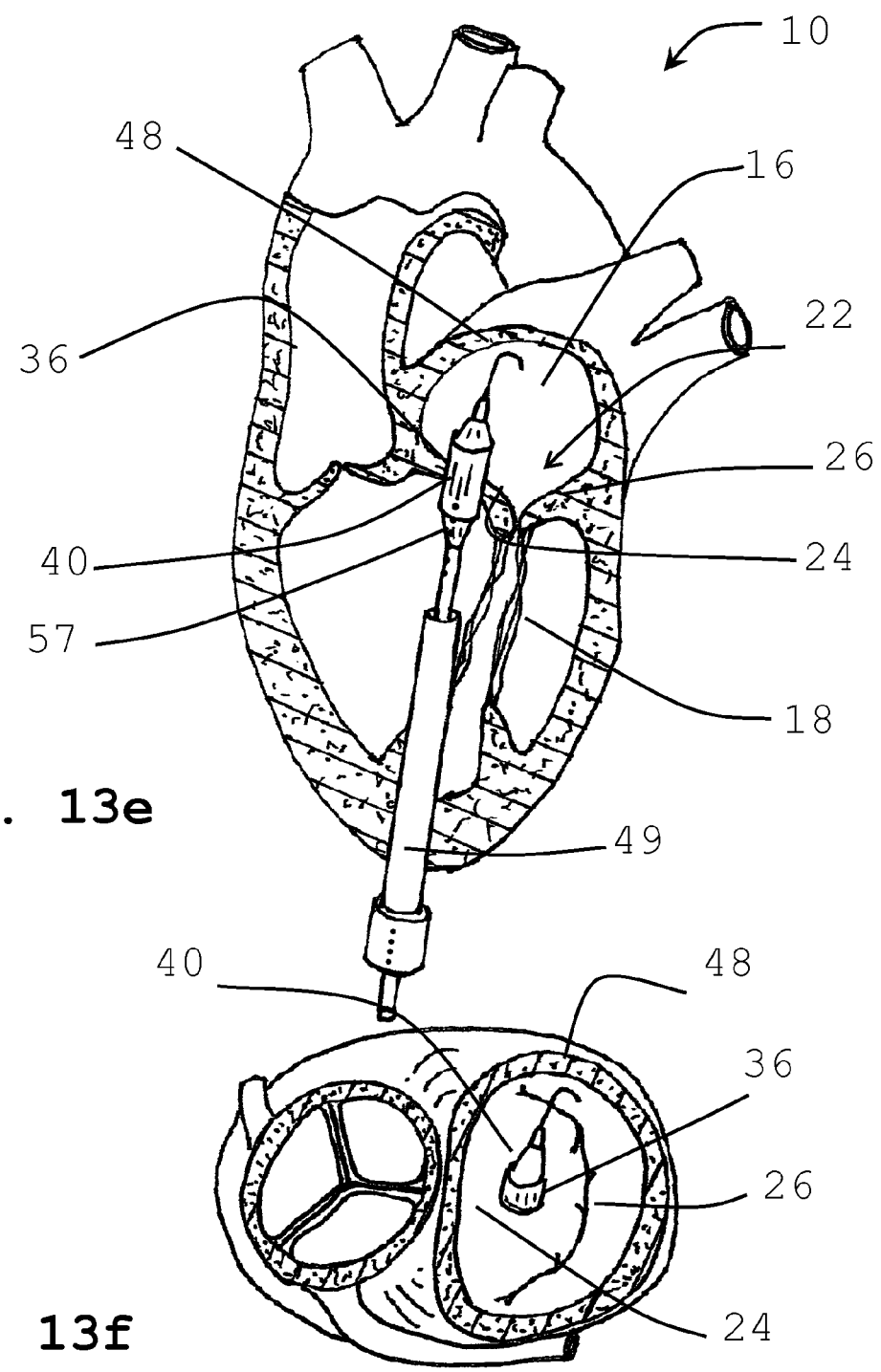
Figures 13G, 13H:
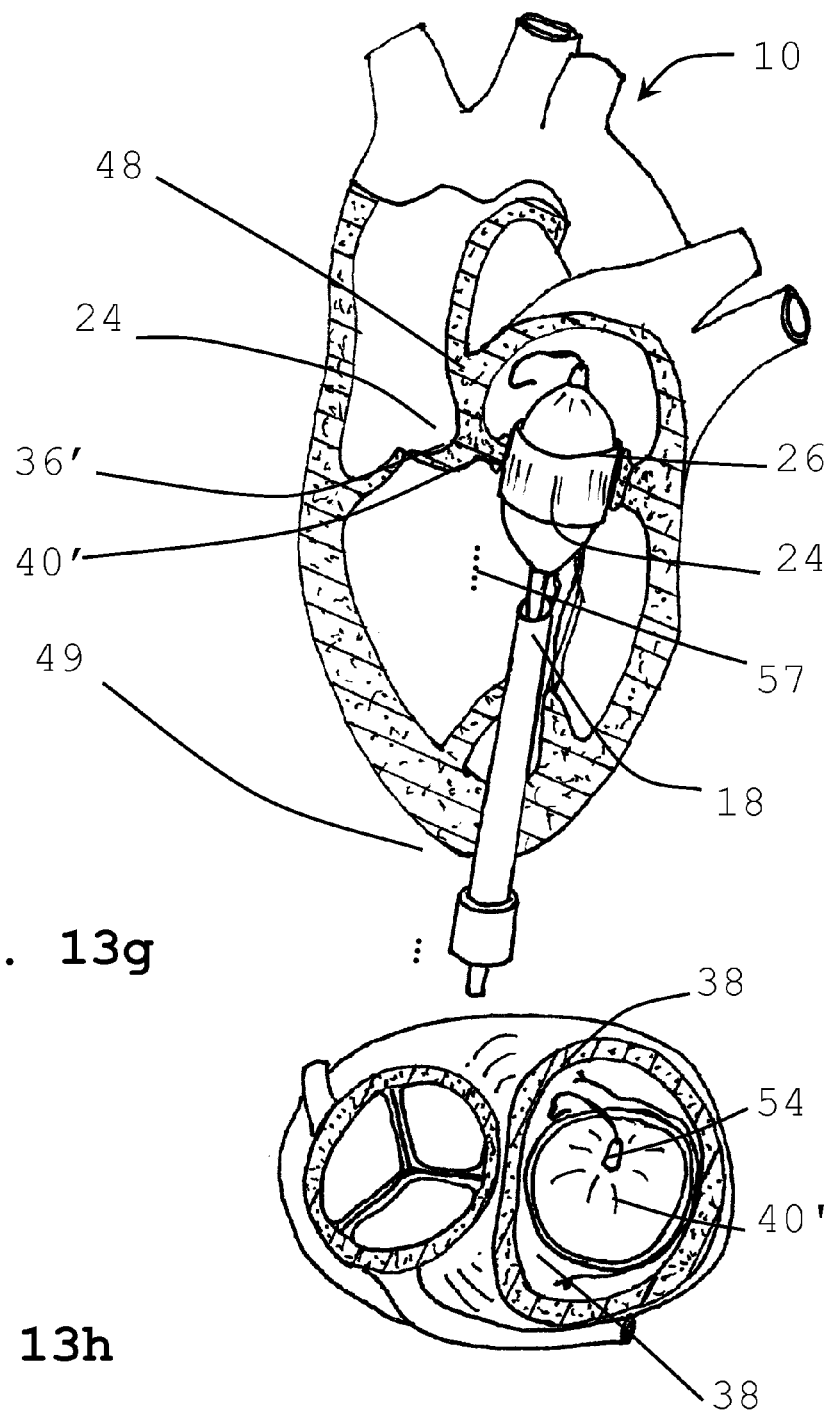
Figure 13I:
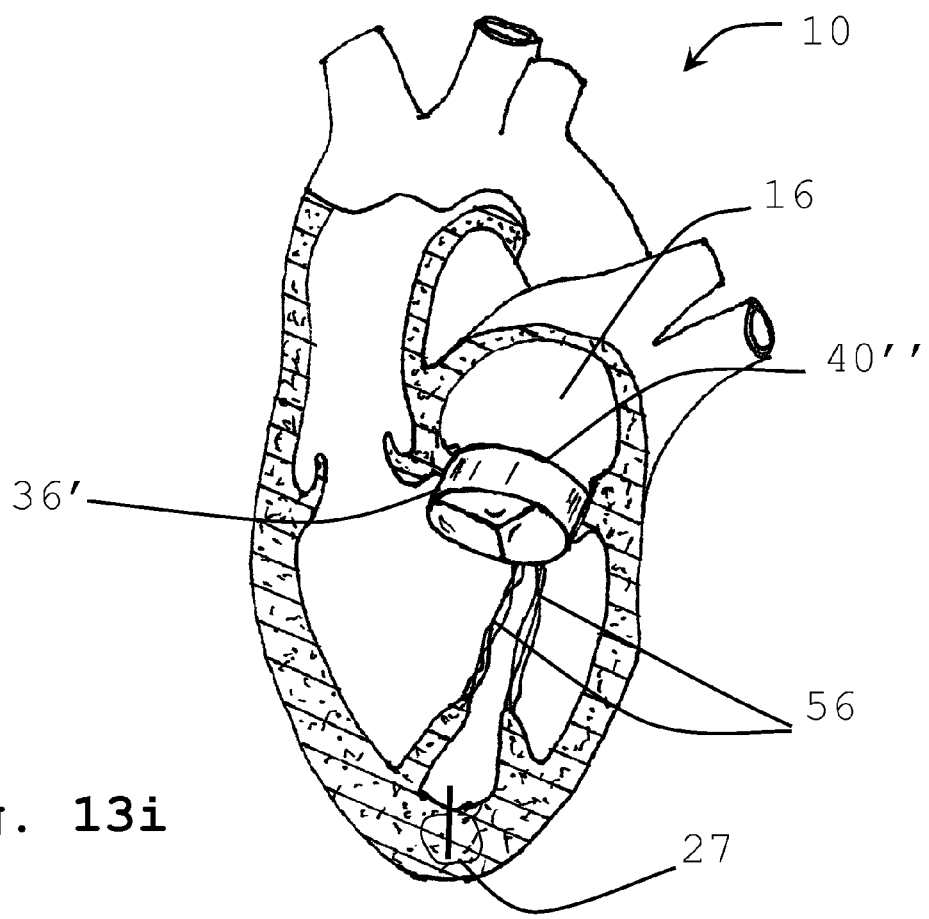
Figure 13J:
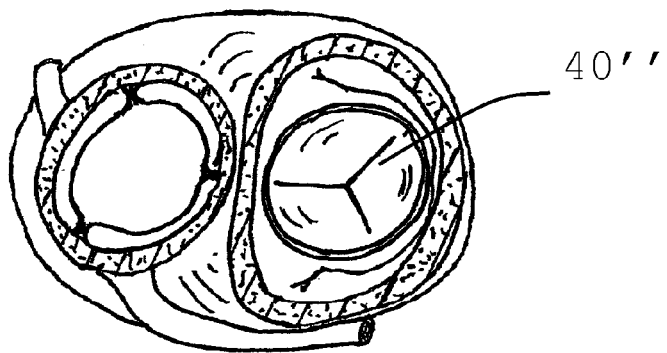

Then the prosthetic valve apparatus 40 (FIG. 13*e*), in its collapsed configuration, mounted on a delivery catheter 57, is tracked over the guide wire 48, to the implantation position in the novel orifice 36, the prosthetic valve being a self expandable valve or a balloon expandable valve as shown in FIGS. 13*e* and 13*f*—step O. Once the valve 40 is positioned within the novel orifice 36', it is expanded—Step Q. The expanded prosthetic valve 40' (FIG. 13*g*) forces the outer edge of the anterior leaflet 24 (FIG. 13*g, h*) against the posterior leaflet 26 (FIGS. 13*g*, 13*h*), thereby cancelling or minimizing natural opening and closing of the mating edges 38 (FIG. 13*h*) of leaflets. The prosthetic valve 40' (FIGS. 13*g*, 13*h*) provides an alternative channel and valve for allowing blood to be pumped from left atrium 16 (FIG. 1) to left ventricle 18 (FIG. 1) on diastole and inhibiting back-flow therebetween in systole. Next the catheter 57 is extracted—step R, freeing the prosthetic apparatus 40" (FIG. 13*i*, 13*j*), which remains securely wedged in the novel orifice 36' (FIGS. 13*i*, 13*j*) It will be noted that as the chordae tendineae 56 (FIG. 13*i*) are not severed, they continue supporting the left ventricle 18 (FIG. 13*i*), and the prosthetic valve 40" (FIG. 13*i*) functions in place of the native valve 22 (FIG. 1). The apex 27 of the heart (FIG. 13*i*) may then be repaired—step S.

Figure 14A:
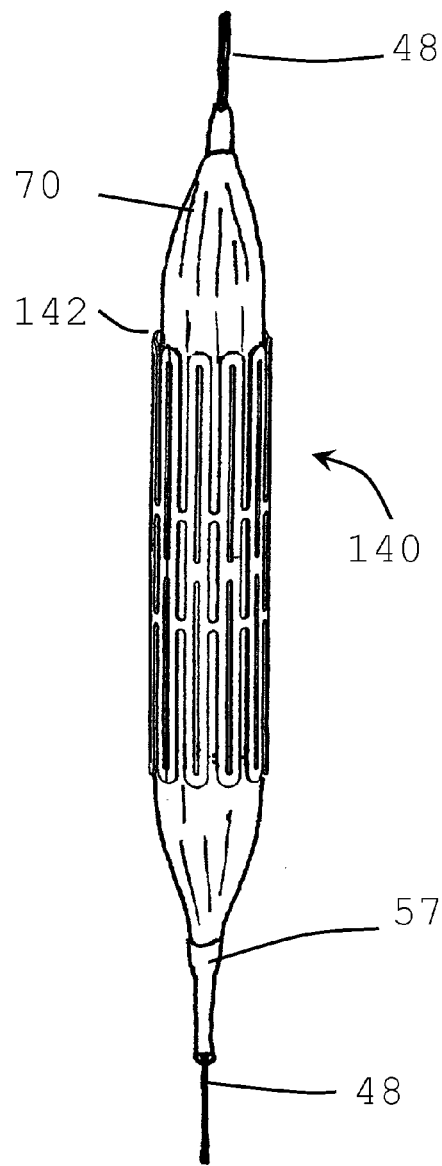
FIGS. 14a and b depict a schematic view of a balloon expandable valve having an indented circumference and a textured surface which assists in securing the valve in its proper position, according to an embodiment of the present invention.
Figure 14B:
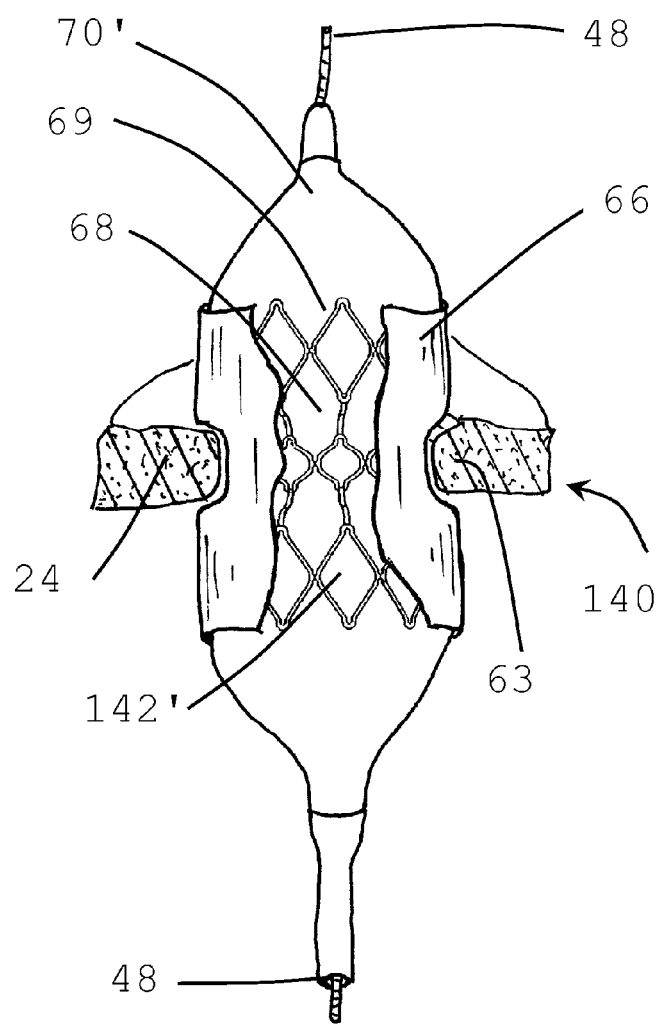

With reference to FIG. 14*a*, the use of a non-self-expandable valve apparatus 140 may be affected by compression of the valve seating 142 of the prosthetic valve apparatus 140 around an expansion arrangement such as a balloon catheter 57—seen here over a guide wire 48. Usefully the balloon 70 can be inflated by using a liquid that contains a contrast dye so that the shape and position of the balloon 70' (FIG. 14*b*) and valve apparatus 140 may be monitored during implantation using fluoroscopy, for example. With reference to FIG. 14*b* as stated previously, preferably the expandable seating 142' is covered with a fabric 66 that promotes tissue growth (fabric 66 is not seen in FIG. 14*a* for clarity purposes). A special design of the seating can be seen in FIG. 14*b*, by cutting the seating with non equal spacing 68 and 69 a shoulder, or dent 63 is created improving the hold and mounting of the valve 140 on the expansion site tissue, in this case the anterior leaflet 24.

With reference to FIGS. 15*a*, 15*b* and 15*c* when using a self-expandable valve seating 242, a catheter with an expansion arrangement is not required. In such instances the valve seating 242 is provided in its collapsed state 242*a* (FIG. 15*a*) and may be inserted within an over tube 60, typically made from plastic or metal, from which the valve 245 is ejected on implantation. Where the self-expandable seating 242 is fabricated from a shape memory metal, it may be configured into its collapsed state by cooling, by immersion in ice water, for example, and/or radially forced to its collapsed state by a crimping tool.

The primary attachment mechanism of the prosthetic valve 245 to the tissue in circumference of the novel orifice 36' is friction. This friction is generated by radial contact forces between the tissue of the orifice 36' and the frame of the valve seating 242 of the prosthetic valve 245. This is typically aided and abetted by fabric cover 66 and the expandable valve seating 242 may further comprise different embodiments such as attachment means for affixing the expandable valve seating 242 to the novel orifice 36'. For example, according to one embodiment of the invention as shown in FIG. 15, the attachment means include a plurality of self expandable barbs 65 which are held in the crimped configuration by the over tube 60 (FIG. 15*a*), after the over tube is inserted through the valve leaflet 24 (FIG. 15*b*), it is pulled back exposing the first row of barbs 65' and allowing them to expand and create a shoulder which helps anchoring the valve 245 in its position within the orifice 36', thereby affixing the valve seating 242 thereto. FIG. 15*c* depicts the last stage of deployment, when the over tube 60 (not seen in FIG. 15*c*) is totally pulled back allowing the second row of barbs 65" to expand and the valve to expand to its full diameter 245. Alternatively, the attachment means may comprise adhesives, nits, magnets, hooks, pins, clips, staples, and the like. Additionally or alternatively, as shown in FIG. 14*b*, the attachment means may be an indent 63 or special profile.

Figure 16:
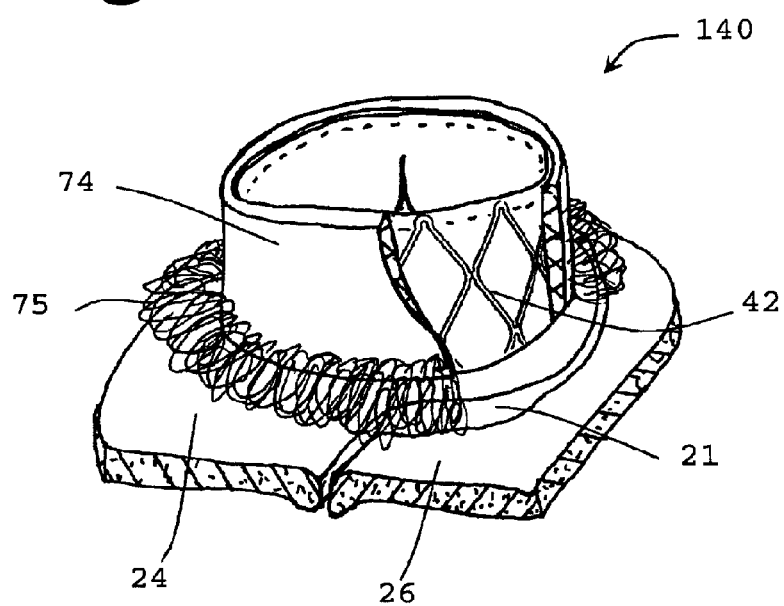
FIG. 16 represents a view of a mitral valve coated by a material which induces and accelerates tissue growth, according to further embodiments of the present invention.

With reference to FIG. 16 a textured surface and/or an artificial fabric 74, which coats the outer circumference of the prosthetic valve 140 and covers the valve seating 42 is shown. An additional portion of fabric 75 is suggested inducing and accelerates tissue growth and helps to secure the valve 140 into the implantation site, functioning in a manner similar to a mitral repair ring, preventing the heart wall from further expanding and assisting in the sealing of the native valve opening 21 and preventing mitral regurgitation. Optionally the circumference of the prosthetic valve seating includes markers which optimize positioning under fluoroscopy.

Figure 17:
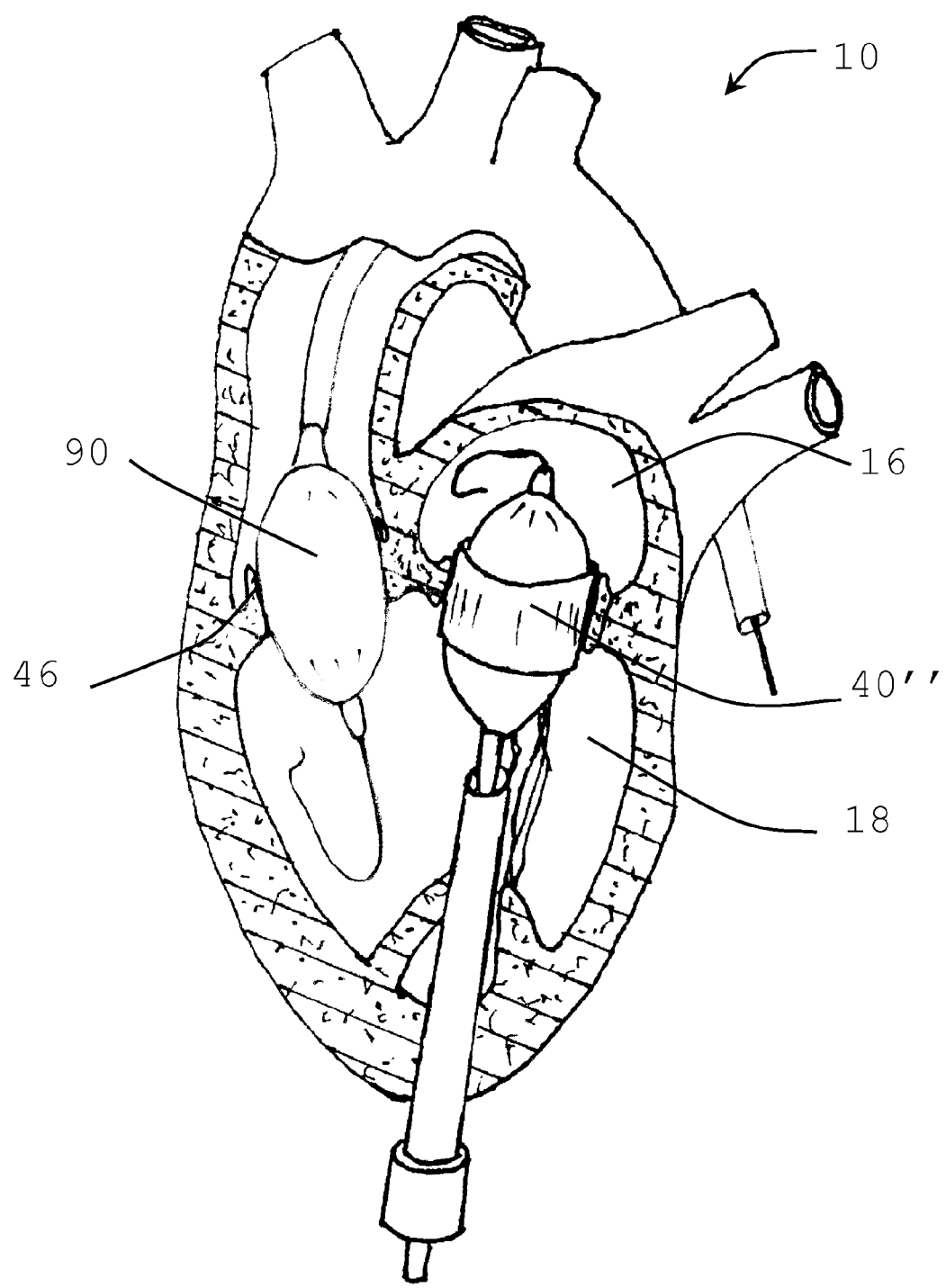
FIG. 17 illustrates a means of positioning the prosthetic mitral valve in the implant site according to another embodiment of the present invention.

Reference is now made to FIG. 17 which describes a solution to another core problem of positioning a prosthetic valve 40" within the beating heart 10. In order to be able to inflate a balloon which blocks the blood passage in the heart it is possible to temporarily stop the blood pressure by pacing the heart to a very high heart rate and thus causing very low blood pressure, or alternatively to apply drugs which temporarily stop the heart. In addition in order to preserve the correct heart geometry and prevent the aortic valve and annulus from collapsing, it is here suggested to inflate a balloon 90 inside the aortic valve 46, and only then to expand the mitral valve. This technique ensures preservation of the heart shape and geometry.

Novel surgical procedures are thus disclosed for implanting a prosthetic valve apparatus that may be as known in the art, which permits implantation thereof without major invasive surgical intervention, such as by using a catheter technique. These minimally invasive procedures and flexibility of methodology will generally make it possible for the patient to resume a substantially normal life. The methods may utilize a known prosthetic valve apparatus, such as one of those referenced hereinabove. Such valves are generally characterized by including a valve seating which is coupled to a one way valve for implantation in the body by means of a technique of catheterization.

The valve seating may be a type of stent which is a radially collapsible and re-expandable cylindrical tube or annular member or mesh sleeve. The collapsible one-way valve is permanently mounted on the valve seating by a suitable technique, such as gluing, welding or by means of a number of suitable sutures.

The valve seating may be comprised of a plurality of strut members having a three-dimensional cage-like structure for engaging the leaflet tissue around the aperture 36, into which the valve seating is inserted. When the valve apparatus is in an expanded configuration, the strut members expand so that the apparatus dynamically conforms to the size and shape of the novel orifice 36' and when the valve apparatus 40 is in its collapsed configuration the strut members are collapsed/folded. The mesh material of the valve seating allows it to compress longitudinally and remain radially crimped while still providing sufficient radial force rigidity such that the valve seating maintains its shape once it has been radially expanded to a desired size.

The expandable valve seating may be made from a biocompatible metallic or polymer material, or a metallic or polymer material that is suitably coated, impregnated, or otherwise treated with a material or combination of materials to impart biocompatibility. The expandable valve seating typically has a semi-rigid or flexible structure, and may be made of a flexible, resiliently yieldable material such as silicone, polytetrafluoroethylene (PTFE), expanded-PTFE (ePTFE), polyurethane, or other polymeric material. It may, however consist of stainless steel or cobalt chrome alloy.

In one embodiment, the expandable valve seating may be made from a super elastic, shape memory material such as Nitinol alloy which can be collapsed to a very small diameter and spring back to a large diameter adequate for a valve orifice cross-section, alternatively it may undergo a phase change as it approaches body temperature and thus reach the desired diameter, it being appreciated that both these characteristics may be combined. In other embodiments, a polymer material may be injected into a different, base material forming the expandable valve seating to impart desired stiffness, flexibility, resilience, or other properties.

Optionally, the expandable valve seating may include biodegradable materials such as biopolymers, thermoplastic starch, polyalctides, cellulose or aliphatic aromatic copolyesters. The expandable valve seating may also be made of a radio-opaque material and/or include radio-opaque markers to facilitate fluoroscopic visualization.

Moreover, the expandable valve seating may be at least partially treated with at least one therapeutic agent. Optionally, the therapeutic agent is eluted into the cardiac tissue or into the cardiac chamber over time. Available therapeutic agents are known to significantly reduce or even prevent a variety of pathological conditions including, but not limited to, arrhythmias, thrombosis, stenosis and inflammation. Accordingly, the therapeutic agent may include at least one of an anti-arrhythmic agent, anticoagulant, an antioxidant, a fibrinolytic, a steroid, an anti-apoptotic agent, and/or an anti-inflammatory agent. Optionally or additionally, the therapeutic agent may be capable of treating or preventing other disease or disease processes such as microbial infections and heart failure. In these instances, the therapeutic agent may include an inotropic agent, a chronotropic agent, an antimicrobial agent, and/or a biological agent such as a cell or protein. A plurality of portions of the present invention may each be separately treated with a different one of the preceding therapeutic agents or other suitable therapeutic agents.

The prosthetic one way valve that is appropriate for use with the present invention which is mounted on the prosthetic valve seating may be made from one or more pieces of biological material formed into a valve having at least one leaflet conduit having dimensions that correspond to the dimensions of the diseased mitral valve. The one-way valve in its open position allows flow to pass through the prosthetic valve from the inlet to the outlet, whereas a reverse flow is prevented due to the collapsible slack portions of the valve assembly that collapse inwardly to block the reverse flow.

Materials of biological origin (e.g., bovine, porcine, equine, ovis aries pericardial tissue) are typically used to construct one-way valves. Specific examples of such prosthetic heart valves are known in the art. The prosthetic one way valve is operatively secured to the expandable valve seating, such as by sutures. Alternatively, the prosthetic valve may be secured to the expandable valve seating in a variety of different manners including, for example, clips, pins, staples, and the like.

The methods of treatment described herein may be advantageous over known methods for a number of reasons. One advantage is that rupture of chordae tendineae may be avoided. In contradistinction to known methods of using prosthetic valves, the apparatus is not inserted via the native valve into the existing native opening. Rather, a new aperture is formed in the anterior leaflet. Another advantage is it offers a novel solution for mitral regurgitation by closing the native valve and creating a new orifice where a new replacement one way valve is implanted which seating is wedged tightly therein. Generally no need for positioning of an annuloplasty ring as preliminary experiments indicate that the new location and method of installation of the prosthetic valve provides enhanced securing in place with reduced risk of displacement over prior art positions and methods. Also there is no need for prior sizing of the apparatus thus rendering the method more cost effective. Thus the method of the present invention provides a solution to the problems of displacement, paravalvular leakage, regurgitation and dilation.

These methods are advantageous as many of the different and available prosthetic valves known in the art, designed for implantation in the body in conventional locations by catheterization may be used in the novel procedure and new location, irrespective of the size and shape of the native valve. Thus the choice of valve is determined by its functionality, cost and availability and is largely independent of the specific patient's heart shape and size.

From the above description of the invention, those skilled in the art will perceive improvements, changes and modifications. Although transvascular approaches are illustrated, the skilled artisan should appreciate that an open surgery approach may be used to replace a diseased cardiac valve by using this method. Any number of attachment means could be provided and configured to anchor in the novel orifice.

Features shown with some specific embodiments may be incorporated with other embodiments. Thus the scope of the present invention is defined by the appended claims and includes both combinations and sub combinations of the various features described hereinabove as well as variations and modifications thereof, which would occur to persons skilled in the art upon reading the foregoing description.

In the claims, the word "comprise", and variations thereof such as "comprises", "comprising" and the like indicate that the components listed are included, but not generally to the exclusion of other components.

The invention claimed is:

1. A method of treating a patient with a dysfunctional or diseased heart valve comprising the steps of:
   (A) performing a preliminary edge to edge procedure to couple leaflets of the heart valve together edge-to-edge;

(B) piercing an aperture through a first leaflet of the valve;
(C) advancing and positioning a collapsed prosthetic valve apparatus comprising a one-way valve mounted on an expandable seating, into the aperture;
(D) expanding the expandable seating and forcing an outer edge of the first leaflet against an outer edge of a second leaflet; the prosthetic valve providing an alternative passageway for blood flow therethrough, whilst inhibiting back-flow in systole.

2. The method of claim 1, wherein said preliminary edge to edge procedure is performed during an earlier procedure, and the present method is a further procedure to further treat the patient.

3. The method of claim 2, wherein said preliminary edge to edge procedure is selected from the group consisting of double orifice repair and paracommissural repair.

4. The method of claim 1, wherein said preliminary edge to edge procedure is selected from the group consisting of suturing, clipping and stapling leaflet edges together.

5. The method of claim 1, wherein said preliminary edge to edge procedure is an Alfieri procedure.

6. The method of claim 1, wherein the valve is a mitral valve.

7. The method of claim 1 wherein said piercing is by a technique selected from the group comprising mechanical tools, laser tools and hot wires.

8. The method of claim 1 wherein said first leaflet is an anterior leaflet.

9. The method of claim 1 further comprising at least one limitation selected from the group comprising:
(i) the first leaflet of the mitral valve is accessed via the left ventricle;
(ii) access is by a transvascular approach route;
(iii) access uses transcatheterization;
(iv) the left ventricle is accessed transapically;
(v) the left ventricle is accessed via the aortic valve.

10. The method of claim 1 wherein the first leaflet of the mitral valve is accessed via right atrium by a transvascular approach.

11. The method of claim 10, using transcatheterization or wherein the right atrium is accessed via vena cava and the left atrium is accessed by piercing septum interatrial.

12. The method of claim 1, wherein the expandable seating has at least one of the following limitations:
(i) said expandable seating is an annular member and the step of expanding the expandable seating comprises inflating a balloon within the annular member;
(ii) the expandable seating comprises a shape memory alloy that expands as it approaches body temperature;
(iii) the expandable seating comprises a super elastic alloy that expands as it released from a constraining tube (over tube);
(iv) the expandable seating is coated with a material which aids tissue growth;
(v) the expandable seating has a textured surface which engages surrounding tissue to secure valve apparatus in place;
(vi) the expandable seating comprises self-expanding shoulders which assist in securing the valve in its proper position.

13. The method of claim 1 comprising a preliminary step selected from the group consisting of:
(a) obtaining regulatory approval for the prosthetic valve for insertion into an aperture made within the first leaflet of the valve;
(b) packaging the prosthetic valve in a package labeled as appropriate for insertion into an aperture made within the first leaflet of the valve;
(c) packaging the prosthetic valve with instructions describing its suitability for insertion into an aperture made within the first leaflet of the valve;
(d) marketing the prosthetic for insertion into an aperture made within the first leaflet of the valve.

14. A method of correcting a heart valve that has been repaired by an edge to edge procedure, comprising the steps of:
(B) piercing an aperture through a first leaflet of the valve;
(C) advancing and positioning a collapsed prosthetic valve apparatus comprising a one-way valve mounted on an expandable seating, into the aperture;
(D) expanding the expandable seating and forcing an outer edge of the first leaflet against an outer edge of a second leaflet; the prosthetic valve providing an alternative passageway for blood flow therethrough, whilst inhibiting back-flow in systole.

15. The method of claim 14, wherein the edge to edge procedure comprises suturing an anterior leaflet to a posterior leaflet to reduce mitral regurgitation.

16. The method of claim 14, wherein the edge to edge procedure comprises clipping an anterior leaflet to a posterior leaflet to reduce mitral regurgitation.

17. The method of claim 14, wherein the edge to edge procedure comprises a paracommissural repair to reduce mitral regurgitation.

18. The method of claim 14 comprising a preliminary step selected from the group consisting of:
(a) obtaining regulatory approval for the prosthetic valve for insertion into an aperture made within the first leaflet of the valve;
(b) packaging the prosthetic valve in a package labeled as appropriate for insertion into an aperture made within the first leaflet of the valve;
(c) packaging the prosthetic valve with instructions describing its suitability for insertion into an aperture made within the first leaflet of the valve;
(d) marketing the prosthetic for insertion into an aperture made within the first leaflet of the valve.

19. A method of repairing a dysfunctional or diseased heart valve comprising the steps of:
(B) piercing an aperture through a first leaflet of the valve;
(C) advancing and positioning a collapsed prosthetic valve apparatus comprising a one-way valve mounted on an expandable seating, into the aperture;
(D) expanding the expandable seating and forcing an outer edge of the first leaflet against an outer edge of a second leaflet; the prosthetic valve providing an alternative passageway for blood flow therethrough, whilst inhibiting back-flow in systole, and
(E) joining edges of a first leaflet to a second leaflet.

20. The method of claim 19 wherein said joining is selected from the group consisting of suturing, clipping and stapling.

* * * * *